US009572723B2

United States Patent
Schneider et al.

(10) Patent No.: US 9,572,723 B2
(45) Date of Patent: *Feb. 21, 2017

(54) METHOD AND APPARATUS FOR CHANGING THE ORIENTATION OF AN ABSORBENT ARTICLE

(71) Applicant: The Procter & Gamble Company, Cincinnati, OH (US)

(72) Inventors: Uwe Schneider, Cincinnati, OH (US); Todd Douglas Lenser, Liberty Township, OH (US); Clifford Theodore Papsdorf, Loveland, OH (US)

(73) Assignee: The Procter & Gamble Plaza, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/837,004

(22) Filed: Aug. 27, 2015

(65) Prior Publication Data

US 2015/0366721 A1 Dec. 24, 2015

Related U.S. Application Data

(63) Continuation of application No. 14/038,821, filed on Sep. 27, 2013, now Pat. No. 9,150,321.

(Continued)

(51) Int. Cl.
*B65G 47/24* (2006.01)
*A61F 13/15* (2006.01)
(Continued)

(52) U.S. Cl.
CPC ... *A61F 13/15764* (2013.01); *A61F 13/15747* (2013.01); *B65B 63/00* (2013.01); *B65G 47/244* (2013.01); *B65G 47/848* (2013.01)

(58) Field of Classification Search
CPC ............... B65H 2801/57; B65H 2301/33216; B65G 29/00; B65G 47/244; B65G 47/848; B65B 63/00; A61F 13/15764
(Continued)

(56) References Cited

U.S. PATENT DOCUMENTS 3,677,389 A * 7/1972 Benatar ............... B65G 17/005
                                                      198/374
3,860,003 A    1/1975 Buell
(Continued)

FOREIGN PATENT DOCUMENTS

EP    0 582 963 A1    2/1994
EP    1 062 929 A1   12/2000
(Continued)

OTHER PUBLICATIONS

U.S. Appl. No. 14/038,828, filed Sep. 27, 2013, Uwe Schneider.
(Continued)

*Primary Examiner* — James R Bidwell
(74) *Attorney, Agent, or Firm* — Sarah M. DeCristofaro; Abbey A. Lopez

(57) ABSTRACT

The methods and apparatuses disclosed herein operate to change the orientation of an absorbent article. The apparatus includes a transfer apparatus having a frame that is rotatable about a first axis of rotation and a transfer member that is rotatable about a second axis of rotation. The method includes advancing an absorbent article in a machine direction. The absorbent article is defined by a longitudinal centerline intersected by a lateral centerline at a center. The method includes rotating the absorbent article from a first orientation where the longitudinal centerline extends in a cross direction to a second orientation where the longitudinal centerline extends in the machine direction. The method includes shifting the absorbent article such that the center of
(Continued)

the absorbent article shifts from a first cross-directional position to a second cross-directional position. The steps of rotating the absorbent article and shifting the absorbent article may occur concurrently.

20 Claims, 25 Drawing Sheets

Related U.S. Application Data

(60) Provisional application No. 61/717,274, filed on Oct. 23, 2012.

(51) Int. Cl.
*B65B 63/00* (2006.01)
*B65G 47/84* (2006.01)
*B65G 47/244* (2006.01)

(58) Field of Classification Search
USPC .......................................... 198/411, 400, 414
See application file for complete search history.

(56) References Cited

U.S. PATENT DOCUMENTS

| | | | |
|---|---|---|---|
| 4,085,839 A * | 4/1978 | Crawford | B65G 47/2445 198/410 |
| 4,695,278 A | 9/1987 | Lawson | |
| 4,704,115 A | 11/1987 | Buell | |
| 4,795,454 A | 1/1989 | Dragoo | |
| 4,909,803 A | 3/1990 | Aziz et al. | |
| 4,967,899 A * | 11/1990 | Newsome | B65G 47/2445 198/411 |
| 5,967,292 A * | 10/1999 | Corrales | B65G 47/244 198/379 |
| 5,988,354 A * | 11/1999 | Spatafora | B65G 29/00 198/374 |
| 6,248,195 B1 | 6/2001 | Schmitz | |
| 6,523,035 B1 | 2/2003 | Fleming et al. | |
| 6,546,987 B1 | 4/2003 | Tachibana et al. | |
| 6,568,524 B1 * | 5/2003 | Cornell | B65G 47/086 198/411 |
| 6,776,316 B2 | 8/2004 | Van Eperen et al. | |
| 7,383,865 B2 | 6/2008 | Umebayashi et al. | |
| 7,569,039 B2 | 8/2009 | Matsuda et al. | |
| 8,011,493 B2 * | 9/2011 | Giuliani | B65G 47/244 198/406 |
| 8,870,732 B2 | 10/2014 | Schneider et al. | |
| 9,150,321 B2 * | 10/2015 | Schneider | A61F 13/15764 |
| 2003/0062113 A1 | 4/2003 | Van Eperen et al. | |
| 2007/0074953 A1 | 4/2007 | McCabe | |
| 2007/0219521 A1 | 9/2007 | Hird et al. | |
| 2009/0312730 A1 | 12/2009 | LaVon et al. | |
| 2011/0139657 A1 | 6/2011 | Hird et al. | |
| 2011/0139658 A1 | 6/2011 | Hird et al. | |
| 2011/0139659 A1 | 6/2011 | Hird et al. | |
| 2011/0139662 A1 | 6/2011 | Hird et al. | |
| 2011/0152812 A1 | 6/2011 | Hird et al. | |
| 2011/0247747 A1 | 10/2011 | Schneider et al. | |
| 2011/0251038 A1 | 10/2011 | LaVon et al. | |
| 2012/0021186 A1 | 1/2012 | Schneider | |
| 2012/0061015 A1 | 3/2012 | LaVon et al. | |
| 2012/0061016 A1 | 3/2012 | LaVon et al. | |
| 2013/0153365 A1 | 6/2013 | Schoultz | |
| 2014/0378287 A1 | 12/2014 | Schneider et al. | |

FOREIGN PATENT DOCUMENTS

| | | |
|---|---|---|
| EP | 1 162 162 A1 | 12/2001 |
| EP | 1 947 037 A1 | 7/2008 |
| EP | 2 277 809 A1 | 1/2011 |
| EP | 2 486 904 A2 | 8/2012 |
| JP | 2005000296 A | 1/1996 |
| WO | WO 2007/070113 A1 | 6/2007 |
| WO | WO 2011/127111 | 10/2011 |

OTHER PUBLICATIONS

PCT International Search (PCT/US2013/065999) Report dated Jan. 7, 2014, 10 pages.
PCT International Search (PCT/US2013/065872) Report dated Jan. 7, 2014, 10 pages.

\* cited by examiner

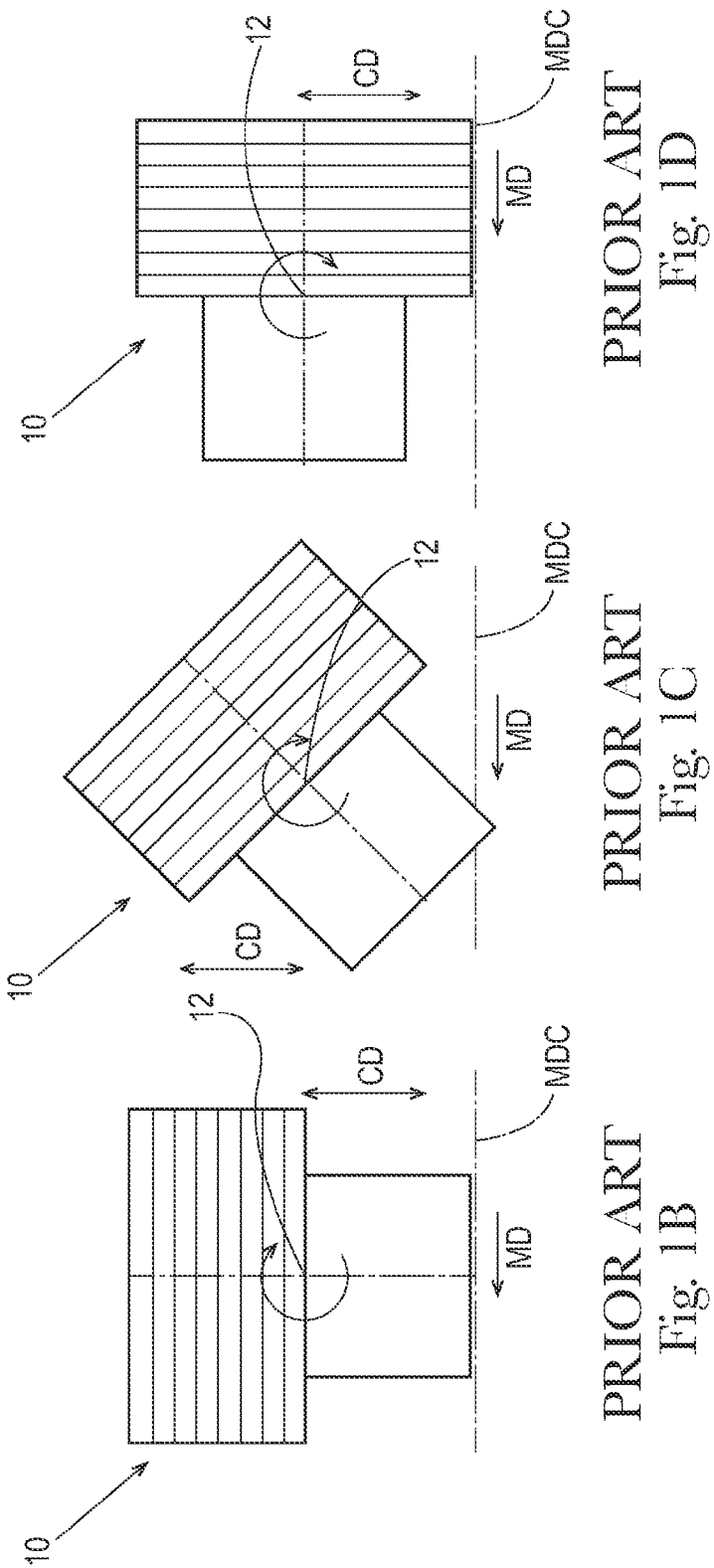

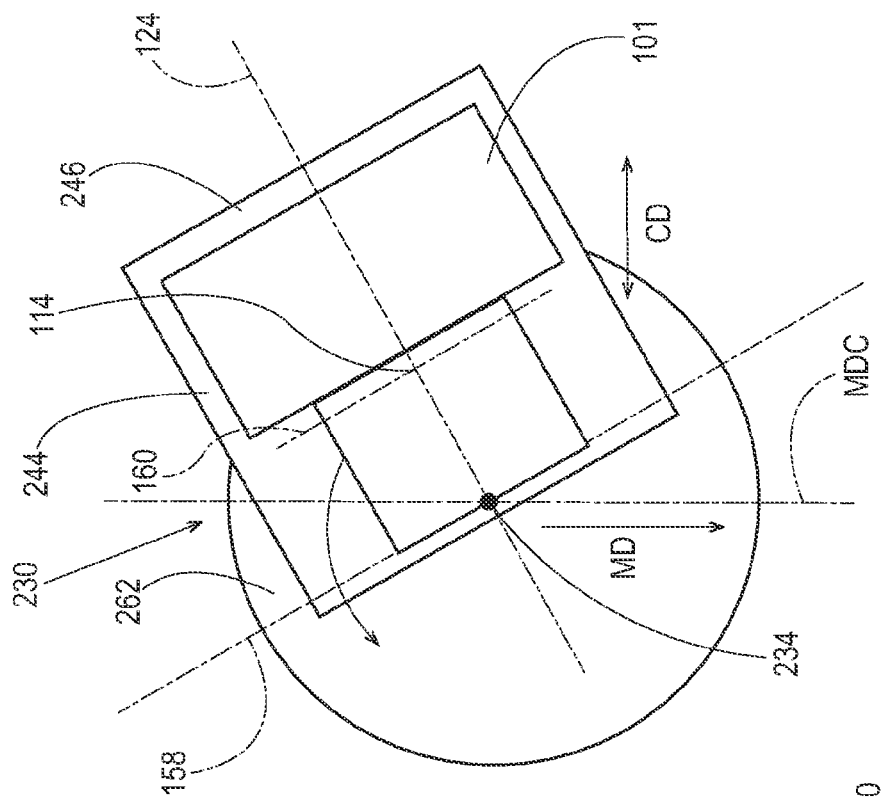
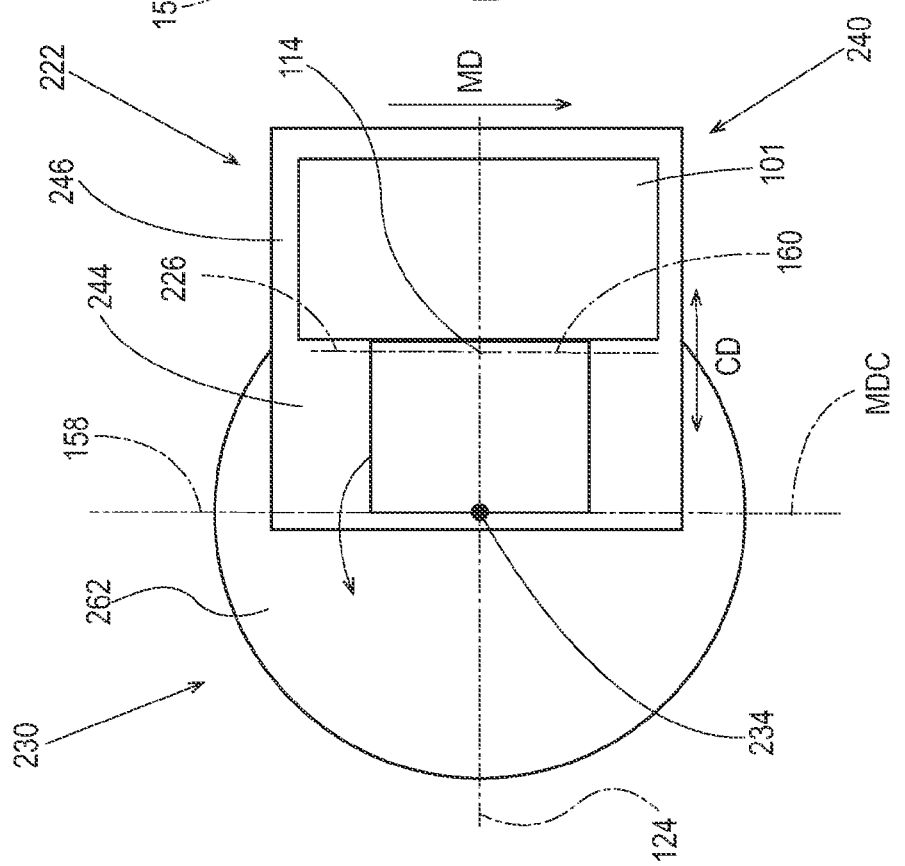
Fig. 11A
Fig. 11B

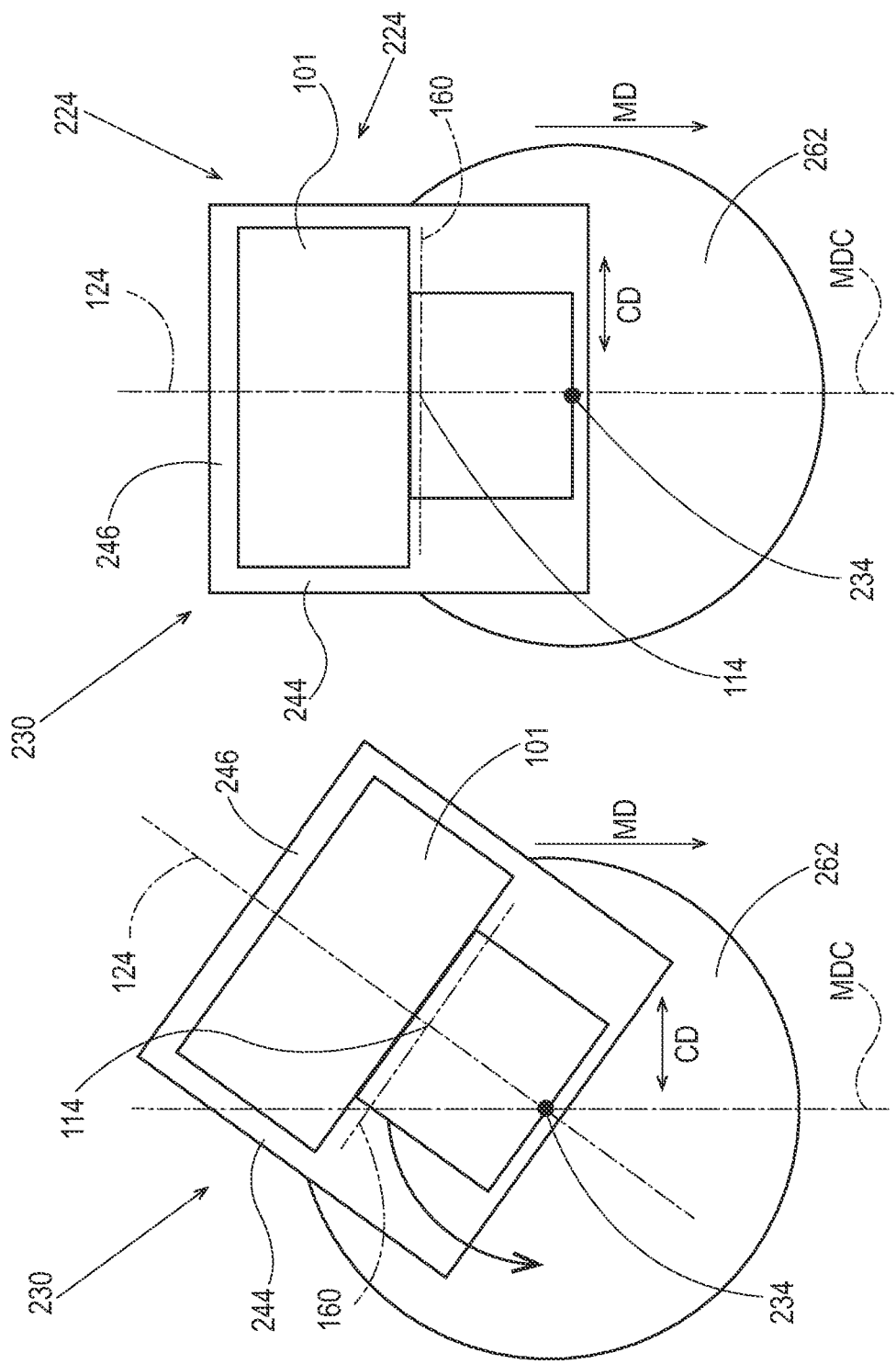

METHOD AND APPARATUS FOR CHANGING THE ORIENTATION OF AN ABSORBENT ARTICLE

CROSS REFERENCE TO RELATED APPLICATION

This application is a continuation of Ser. No. 14/038,821 filed on Sep. 27, 2013, which claims the benefit of U.S. Provisional Application No. 61/717,274 filed on Oct. 23, 2012, the substance of which are incorporated herein by reference.

FIELD OF THE INVENTION

The present disclosure relates to methods and apparatuses for manufacturing absorbent articles, and more particularly, to methods and apparatuses for changing the orientation of an absorbent article.

BACKGROUND OF THE INVENTION

Along an assembly line, various types of articles, such as diapers and other absorbent articles, may be assembled by adding components to and/or otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing webs and component parts are subjected to a final knife cut to separate the webs into discrete diapers or other absorbent articles.

With reference to FIG. 1A, in some converting processes, discrete chassis 14 spaced apart from each other are advanced in a machine direction MD and are arranged with a longitudinal centerline 16 parallel with the cross direction CD. The discrete chassis 14 may be positioned such that a lateral centerline 18 of the chassis 14 is aligned with a machine direction centerline MDC. Opposing waist regions of the discrete chassis 14 may be joined with continuous lengths of elastically extendable front and back waistband webs advancing in the machine direction. While connected with the chassis 14, the front and back waistband webs may be maintained in a fully stretched condition along the machine direction MD, forming a continuous length of absorbent articles. The continuous length of absorbent articles may then be folded in a cross direction CD. During the folding process in some converting configurations, one of the front and back waistband webs is folded 180° into a facing relationship with the opposing waistband. The continuous length of absorbent articles may be cut into discrete absorbent articles 10, such as shown in FIG. 1A, and advanced to a packaging operation.

As a result of folding the absorbent articles 10 180° in the cross direction CD, in some converting configurations, a center 12 of the folded, discrete absorbent article 10 is offset from the machine direction centerline MDC as shown in FIG. 1B. In some processes, it may be necessary to rotate the folded, discrete absorbent article 10 in order to change the orientation of the discrete absorbent article 10 for downstream processing, such as packaging. However, some processes for rotating a discrete absorbent article 10 are configured to rotate the discrete absorbent article 10 about the center 12 of the discrete absorbent article 10 as shown in FIGS. 1B-1D. As a result, the center 12 of the folded discrete absorbent article 10 may be offset from the machine direction centerline MDC as shown in FIG. 1D. Consequently, it may be necessary to position downstream equipment off center from the machine direction centerline MDC in order to advance the folded discrete absorbent articles 10 along a centerline of the downstream equipment. However, due to size and space constraints in some converting operations, it may not be feasible to position equipment away from the machine direction centerline MDC.

Therefore, it would be beneficial to provide a process and apparatus for rotating and shifting a discrete absorbent article such that the discrete absorbent article is aligned with a machine direction centerline.

SUMMARY OF THE INVENTION

In some aspects, the present disclosure includes a method for changing the orientation of an absorbent article, the absorbent article defining a longitudinal centerline that intersects a lateral centerline at a center of the absorbent article, the method comprising the steps of: advancing the absorbent article in a first direction, wherein the absorbent article is oriented such that the longitudinal centerline extends in a second direction that is different from the first direction; positioning the absorbent article on a transfer member configured to rotate about a second axis of rotation, wherein the transfer member comprises a rotation member and a receiving surface attached to a portion of the rotation member, and wherein a center of the rotation member is aligned with the second axis of rotation, and wherein a center of the receiving surface and the center of the absorbent article is offset from the center of the rotation member; rotating the absorbent article about the second axis of rotation such that the longitudinal centerline extends in the first direction; and shifting the absorbent article such that the center of the absorbent article shifts in the second direction.

In some aspects, the present disclosure includes a method for rotating a transfer apparatus about a first axis of rotation. The transfer apparatus comprises a transfer member. The method includes the steps of: advancing the absorbent article in a first direction, wherein the absorbent article is oriented such that the longitudinal centerline extends in a second direction that is different from the first direction; positioning the absorbent article on the transfer member configured to rotate about a second axis of rotation, wherein the transfer member comprises a rotation member and a receiving surface attached to a portion of the rotation member, and wherein a center of the rotation member is aligned with the second axis of rotation, and wherein a center of the receiving surface and the center of the absorbent article is offset from the center of the rotation member; radially displacing the transfer member with respect to the first axis of rotation as the transfer member rotates about the first axis of rotation; rotating the absorbent article about the second axis of rotation such that the longitudinal centerline extends in the first direction; and shifting the absorbent article such that the center of the absorbent article shifts in the second direction.

In some aspects, the present disclosure includes a method for changing the orientation of an absorbent article, the absorbent article defining a longitudinal centerline that intersects a lateral centerline at a center of the absorbent article, the method comprising the steps of: rotating a transfer apparatus about a first axis of rotation, wherein the transfer apparatus comprises a transfer member; advancing the absorbent article in a first direction, wherein the absorbent article is oriented such that the longitudinal centerline extends in a second direction that is different from the first direction; positioning the absorbent article on the transfer member configured to rotate about a second axis of rotation, wherein the transfer member comprises a rotation member and a receiving surface attached to a portion of the rotation member, and wherein a center of the rotation member is aligned with the second axis of rotation, and wherein a center of the receiving surface and the center of the absorbent article is offset from the center of the rotation member, wherein the transfer apparatus is configured to rotate at a variable angular velocity such that the speed at the receiving surface is variable; rotating the absorbent article about the second axis of rotation such that the longitudinal centerline extends in the first direction; and shifting the absorbent article such that the center of the absorbent article shifts in the second direction.

BRIEF DESCRIPTION OF THE DRAWINGS

FIG. 1B is a schematic, plan view of a folded, discrete absorbent article that is rotated about the center of the folded, discrete absorbent article according to prior art methods.

FIG. 1C is a schematic, plan view of a folded, discrete absorbent article that is rotated about the center of the folded, discrete absorbent article according to prior art methods.

FIG. 1D is a schematic, plan view of a folded, discrete absorbent article that is rotated about the center of the folded, discrete absorbent article according to prior art methods.

FIG. 11A is a schematic, plan view of an exemplary transfer member.

FIG. 11B is a schematic, plan view of an exemplary transfer member.

FIG. 11C is a schematic, plan view of an exemplary transfer member.

FIG. 11D is a schematic, plan view of an exemplary transfer member.

DETAILED DESCRIPTION OF THE INVENTION

Figure 1A:
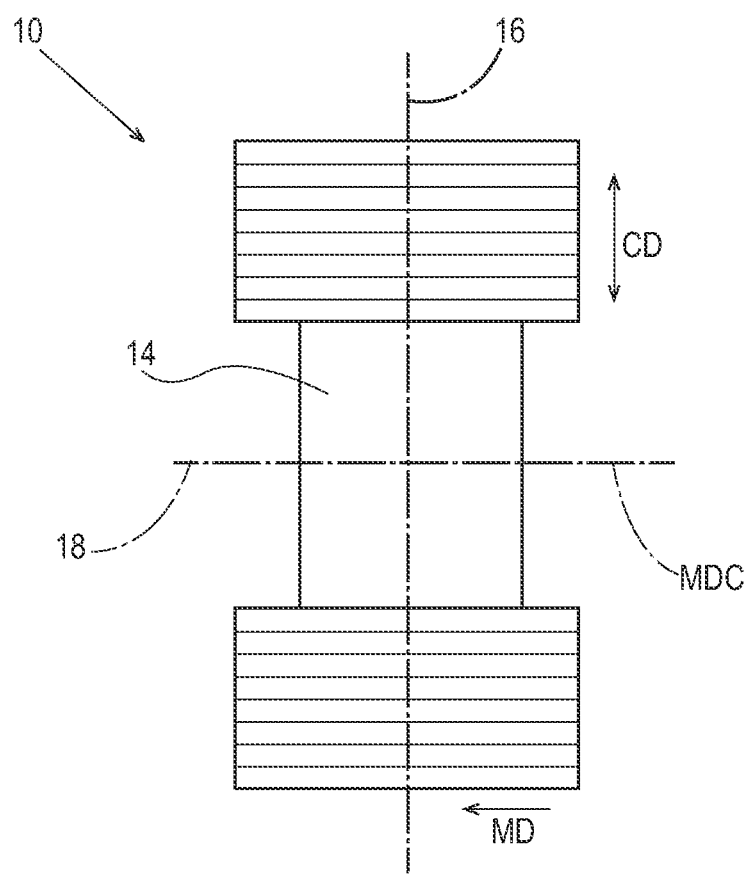
FIG. 1A is a schematic, plan view of a discrete absorbent article.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (for example, they are intended to be discarded after a single use and may also be configured to be recycled, composted or otherwise disposed of in an environmentally compatible manner).

"Joined" is used herein to encompass configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is not parallel with, and usually perpendicular to, the machine direction.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (for example, seams, heat bonds, pressure welds, adhesives, cohesive bonds, mechanical fasteners, etc.). A pant can be preformed anywhere along the circumference of the article in the waist region (for example, side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (for example, seams, heat bonds, pressure welds, adhesives, cohesive bonds, mechanical fasteners, etc.). In addition, pant diapers can be preformed anywhere along the circumference of the waist region (for example, side fastened or connected, front waist fastened or connected, rear waist fastened or connected).

The present disclosure relates to methods and apparatuses for changing the orientation of discrete absorbent articles advancing in a machine direction. The methods and apparatuses discussed herein operate to transfer the folded discrete article from a first carrier apparatus to a second carrier apparatus. The folded discrete article may advance in a first orientation on the first carrier apparatus and may be rotated and shifted to a second orientation and advanced onto the second carrier apparatus using the transfer methods and apparatuses disclosed herein. The folded discrete articles may be defined by a longitudinal centerline and a folded, lateral centerline that intersect at a center of the folded discrete article. In the first orientation, the longitudinal centerline of the folded discrete article may extend in a cross direction and the center may be located at a first cross-directional position. The transfer apparatus operates to rotate and shift the discrete article to the second orientation where the longitudinal centerline of the discrete article extends in the machine direction and the center of the folded discrete article shifts to a second cross-directional position that is different from the first cross-directional position.

The transfer apparatus may include a frame and a plurality of transfer members rotatably connected with the frame. The frame may be configured to rotate about a first axis of rotation and each transfer member may be configured to rotate about a second axis of rotation. The first axis of rotation may extend in a first direction and the second axis of rotation may extend in a second direction that is different from the first direction. A discrete article may advance in the machine direction onto a transfer member of the transfer apparatus. Concurrently, the frame may rotate about the first axis of rotation. As the discrete article advances onto the transfer member, the transfer member may be arranged in a first position and the discrete article may be arranged in a first orientation. The second axis of rotation may be offset from the center of the discrete article. The transfer member rotates the discrete article about the second axis of rotation while the frame continues rotating about the first axis of rotation. As the transfer member rotates about the second axis of rotation, the center of the discrete article shifts in the cross direction. As a result, the transfer member rotates to a second position and the discrete absorbent article shifts to a second orientation. At the second orientation, the longitudinal centerline of the discrete article may extend in the machine direction and the center of the discrete article shifts from a first cross-directional position to a second cross-directional position. However, it is to be appreciated that the discrete absorbent article may be arranged in various configurations at the second orientation depending upon the desired orientation for downstream processing.

While the present disclosure relates to discrete absorbent articles that have been folded about a fold axis that is aligned with a machine direction centerline, it is to be appreciated that the methods and apparatuses described herein may be used to change the orientation of various discrete articles arranged in various configurations. For example, the discrete article may include a fully assembled absorbent article, or the discrete article may include one or more components of an absorbent article. In some exemplary configurations, the discrete article may include a discrete chassis having a topsheet, backsheet, and an absorbent core. The discrete article may be folded, or may be configured in a flat, contracted or uncontracted state. The transfer apparatus may be used to rotate and shift a discrete article in various configurations and orientations.

The processes and apparatuses discussed herein may be used to rotate and shift various types of discrete articles, some of which may be used in the manufacture of different types of absorbent articles. To help provide additional context to the subsequent discussion, the following provides a general description of absorbent articles in the form of diaper pants that may be rotated and shifted in accordance with the methods and apparatuses disclosed herein. While the present disclosure relates to diaper pants, it is to be appreciated that the methods and apparatuses disclosed herein may be used in the manufacture of various types of absorbent articles.

Figure 2:
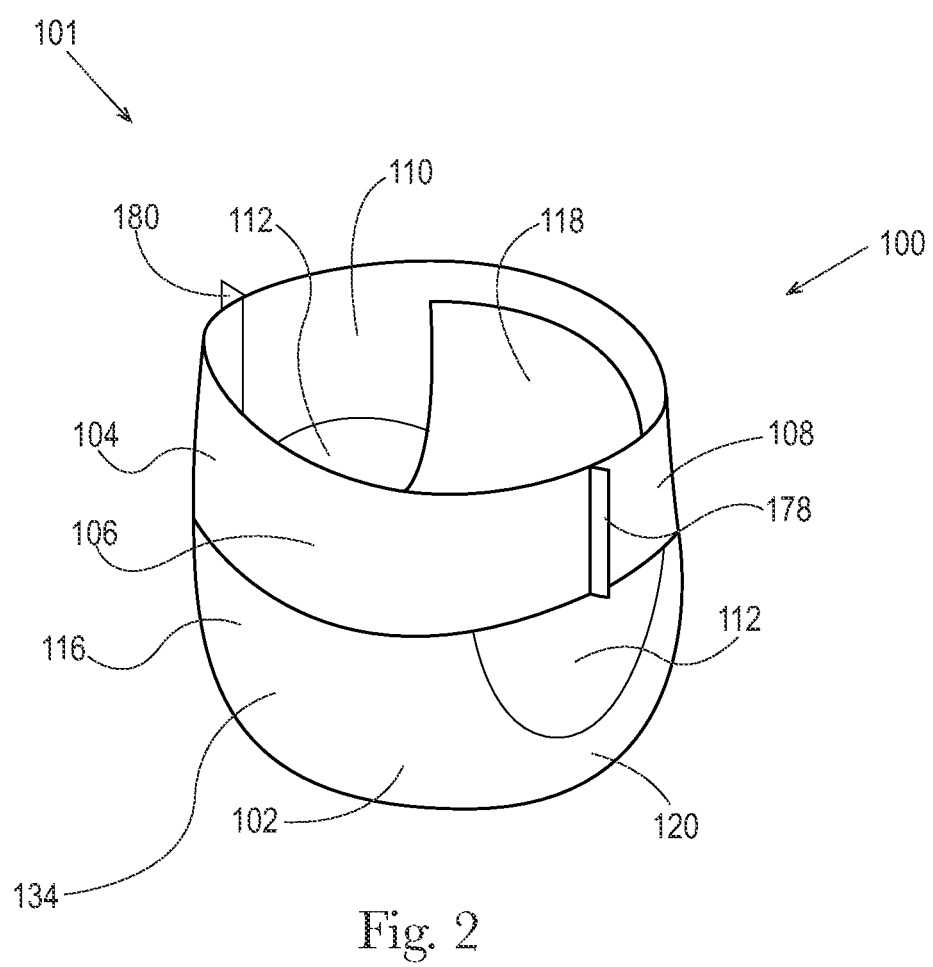
FIG. 2 is a schematic, perspective view of a diaper pant.
Figure 3A:
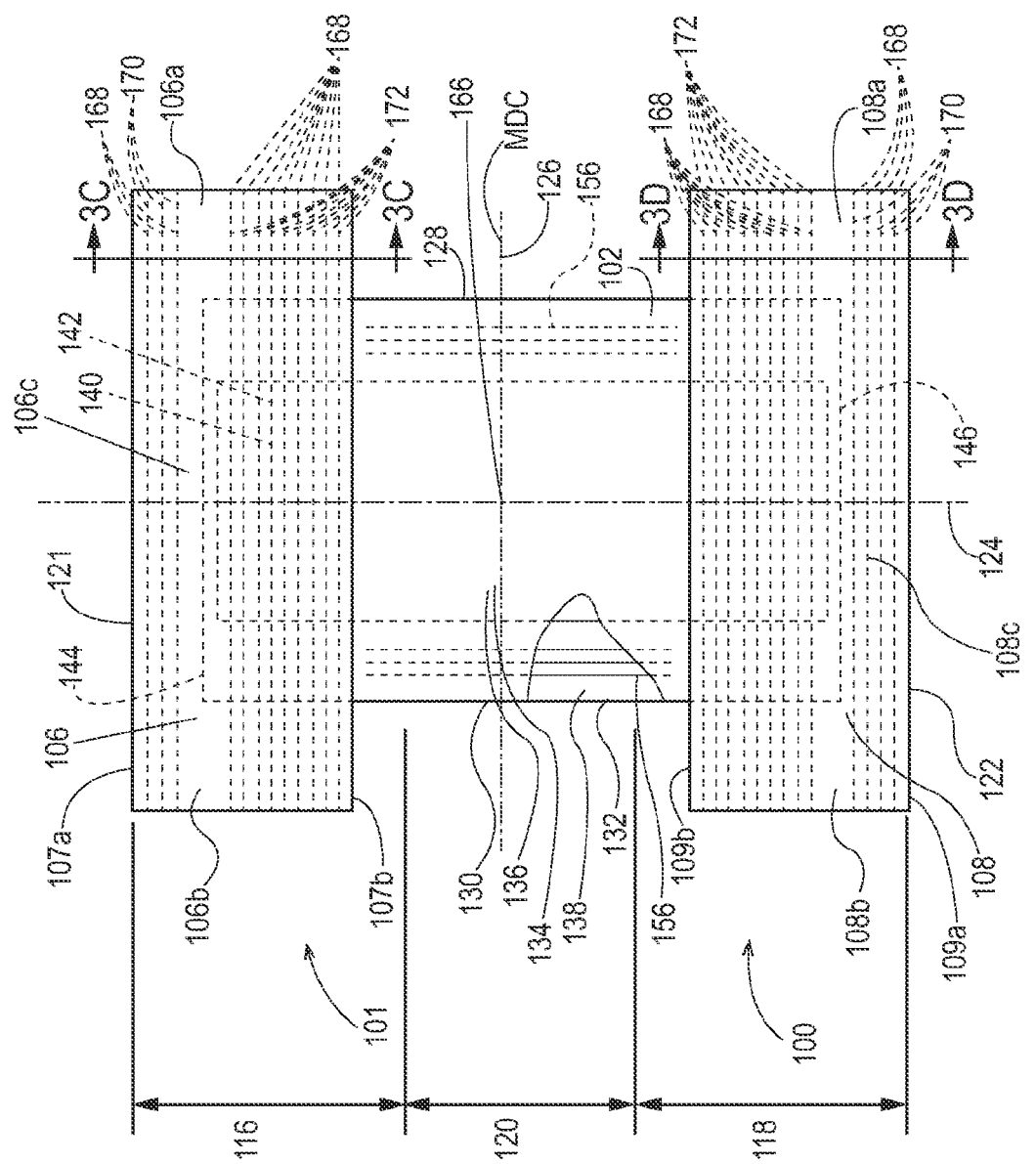
FIG. 3A is a partially cut-away, plan view of a diaper pant.

FIGS. 2 and 3A show examples of an absorbent article 100 in the form of a diaper pant 101 that may be assembled and folded in accordance with the apparatuses and methods disclosed herein. In particular, FIG. 2 shows a perspective view of a diaper pant 101 in a pre-fastened configuration and FIG. 3A shows a plan view of the diaper pant 101 with the portion of the diaper that faces away from a wearer oriented toward the viewer. The diaper pant 101 shown in FIGS. 2 and 3A includes a chassis 102 and a ring-like elastic belt 104. As discussed below in more detail, a first elastic belt 106 and a second elastic belt 108 are connected together to form the ring-like elastic belt 104.

With continued reference to FIG. 3A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region 116, back waist region 118, and crotch region 120 may be one-third of the length of the absorbent article 100. The diaper pant 101 may also include a laterally extending front waist edge 121 in the front waist region 116 and a longitudinally opposing and laterally extending back waist edge 122 in the back waist region 118. To provide a frame of reference for the present discussion, the diaper pant 101 of FIG. 3A is shown with a longitudinal centerline 124 and a lateral centerline 126 that intersect at a center 166 of the extended diaper pant 101. The longitudinal centerline 124 longitudinally bisects the diaper pant 101 such that the longitudinal centerline 124 is equidistant from the chassis side edges 128 and 130. The lateral centerline 126 laterally bisects the diaper pant 101 such that the lateral centerline 126 is equidistant from the front and back waist edges 121 and 122. The center 166 of the extended diaper pant 101 defines a machine direction centerline MDC.

As shown in FIGS. 2 and 3A, the diaper pant 101 may include an inner, wearer facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the absorbent article 100 may also include other features, such as leg elastics and/or leg cuffs to enhance the fit around the legs of the wearer.

As shown in FIG. 3A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 3A, the laterally extending end edges 144 and 146 are located longitudinally inward from the laterally extending front waist edge 121 in the front waist region 116 and the laterally extending back waist edge 122 in the back waist region 118. When the diaper pant 101 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

Referring to FIG. 3A, the diaper pant 101 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695, 278; 4,795,454; 4,704,115; 4,909,803; and U.S. Patent Publication No. 2009/0312730, published on Dec. 17, 2009.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants 101 may have a continuous perimeter waist opening 110 and continuous perimeter leg openings 112 such as shown in FIG. 2.

As previously mentioned, the ring-like elastic belt 104 is defined by a first elastic belt 106 connected with a second elastic belt 108. As shown in FIG. 3A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt 106 is connected with the first waist region 116 of the chassis 102, and the central region 108c of the second elastic belt 108 is connected with the second waist region 118 of the chassis 102. As shown in FIGS. 2 and 3A, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

Figure 3B:
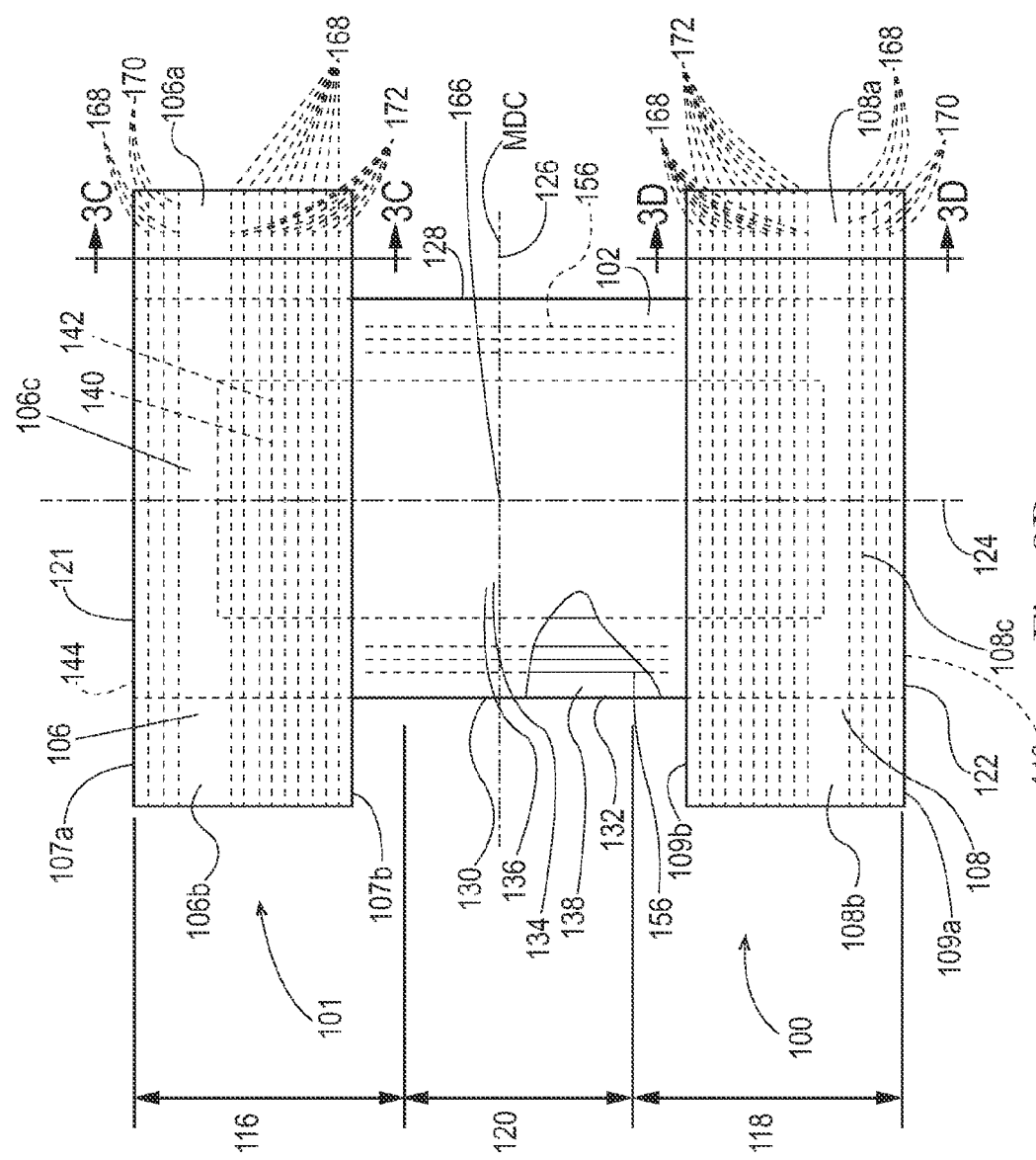
FIG. 3B is a partially cut-away, plan view of a diaper pant.
Figure 3C:
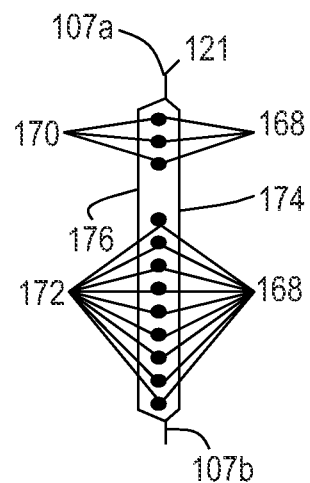
FIG. 3C is a cross-sectional view of the diaper pants of FIGS. 3A and 3B taken along line 3C-3C.
Figure 3D:
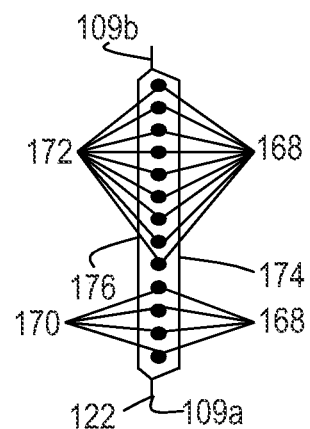
FIG. 3D is a cross-sectional view of the diaper pants of FIGS. 3A and 3B taken along line 3D-3D.

Referring to FIGS. 3A, 3C, and 3D, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt 106 and the second elastic belt 108 may also each include an outer, garment facing layer 176 and an inner, wearer facing layer 174. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (for example, wood or cotton fibers), synthetic fibers (for example, polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 176 and the inner layer 174. The belt elastic material may include one or more elastic elements such as strands, ribbons, or panels extending along the lengths of the elastic belts. As shown in FIGS. 3A, 3C, and 3D, the belt elastic material may include a plurality of elastic strands 168 which may be referred to herein as outer, waist elastics 170 and inner, waist elastics 172. As shown in FIG. 3A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 102 and elastic belts 106, 108 may be configured in different ways other than as depicted in FIG. 3A. For example, FIG. 3B shows a plan view of a diaper pant 101 having the same components as described above with reference to FIG. 3A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (for example, Wiley® mill), and a representative sample of suitable mass taken from the randomly mixed particles.

Figure 4A:
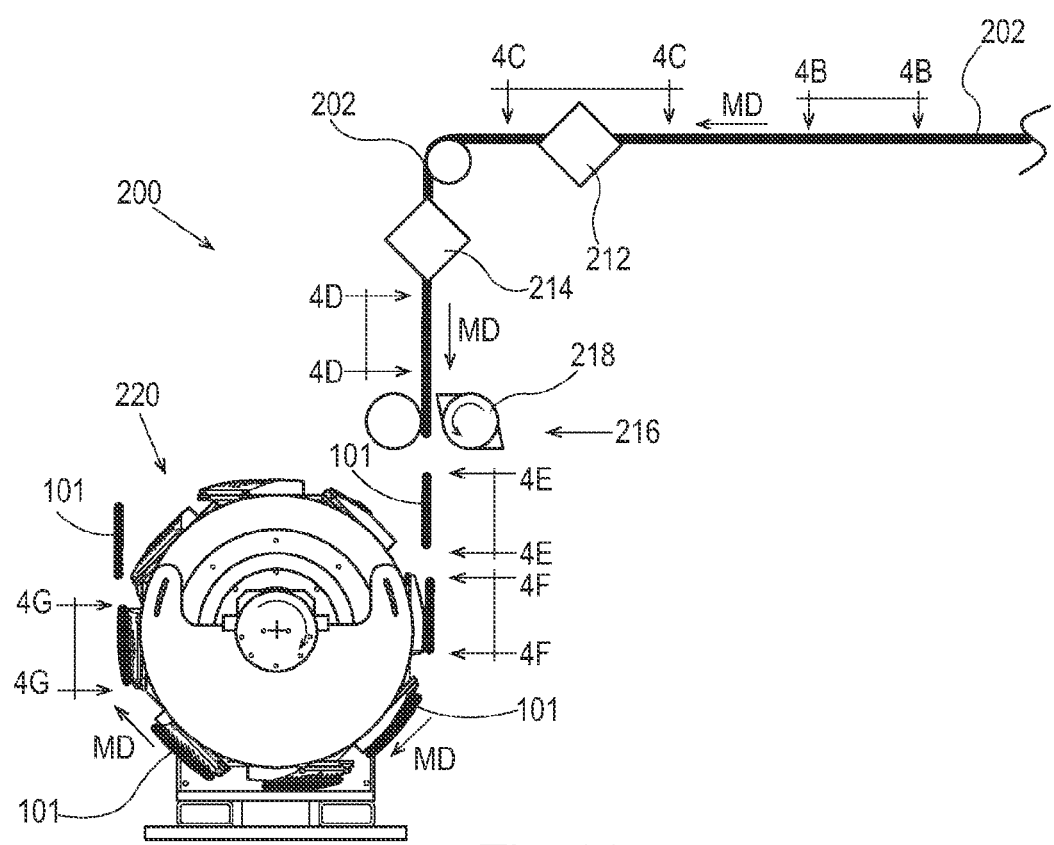
FIG. 4A is a schematic, side view of a converting apparatus adapted to manufacture pre-fastened, pant diapers.

The apparatuses and methods of the present disclosure may be utilized to assemble various components of prefastened, refastenable diaper pants 101. For example, FIG. 4A shows a schematic view of a converting apparatus 200 adapted to manufacture diaper pants 101. The method of operation of the converting apparatus 200 may be described with reference to the various components of the diaper pant 101 described above and shown in FIGS. 2 and 3A. Although the following methods are provided in the context of the diaper pants 101 shown in FIGS. 2 and 3A, it is to be appreciated that various embodiments of diaper pants can be manufactured according the methods disclosed herein, such as for example, the absorbent articles disclosed in U.S. Pat. No. 7,569,039, filed on Nov. 10, 2004; U.S. Pat. No. 7,569,039; U.S. Patent Publication No. 2012/0061016, published on Mar. 15, 2011; and U.S. Patent Publication No. 2012/0061015, published on Mar. 15, 2011.

Figure 4B:
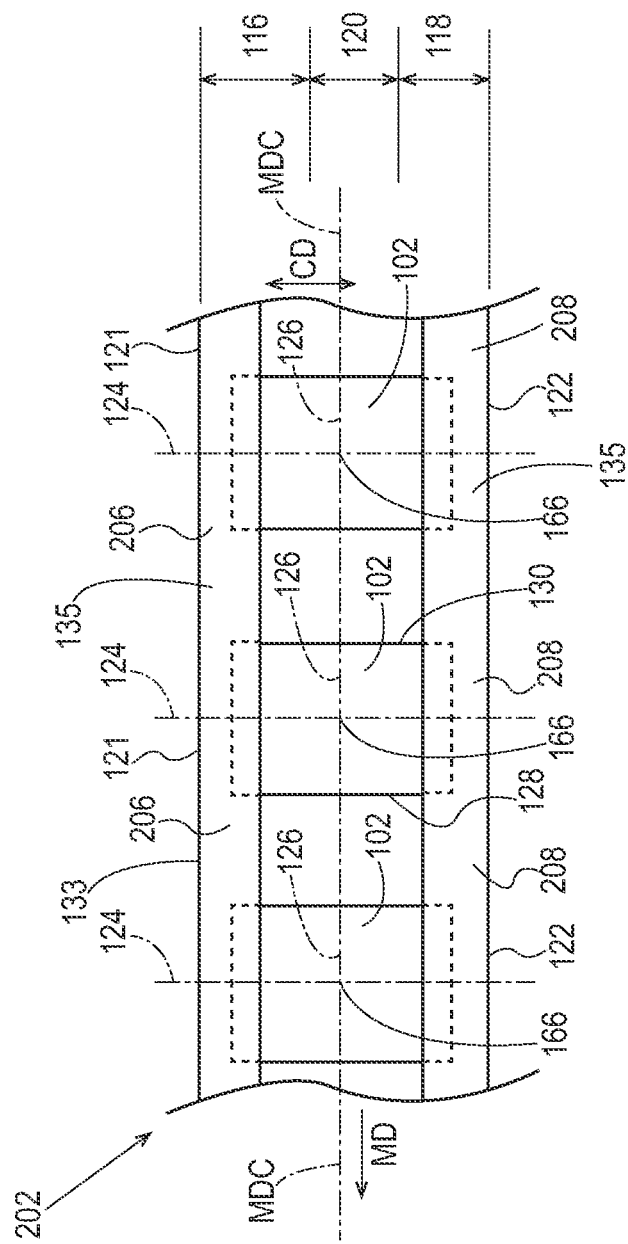
FIG. 4B is a schematic, plan view of a continuous length of diaper pants from FIG. 4A taken along line 4B-4B.

The converting apparatus 200 advances a continuous length of absorbent articles 202 in a first direction, shown as the machine direction MD in FIG. 4A. With reference to FIG. 4B, a continuous length of absorbent articles 202 may be defined by multiple discrete chassis 102 spaced from each other along the machine direction MD and connected with each other by the first and second continuous waistband substrates 206, 208. The continuous length of absorbent articles 202 may be folded in a second direction, shown as the cross direction CD in FIG. 4C, such that the continuous first waistband substrate 206 and the continuous second waistband substrate 208 are in a facing relationship. Next, portions of the first and second continuous waistband substrates 206, 208 may be bonded together. Subsequently, the continuous length of absorbent articles 202 may be cut between the bonded portions of the first and second waistbands 206, 208 to form discrete diaper pants 101. Then, the folded diaper pants 101 may advance to a transfer apparatus 220 where the diaper pants 101 may be rotated and shifted from a first orientation to a second orientation. From the transfer apparatus 220, the folded diaper pant 101 may continue advancing in the machine direction MD to downstream processing.

Figure 4C:
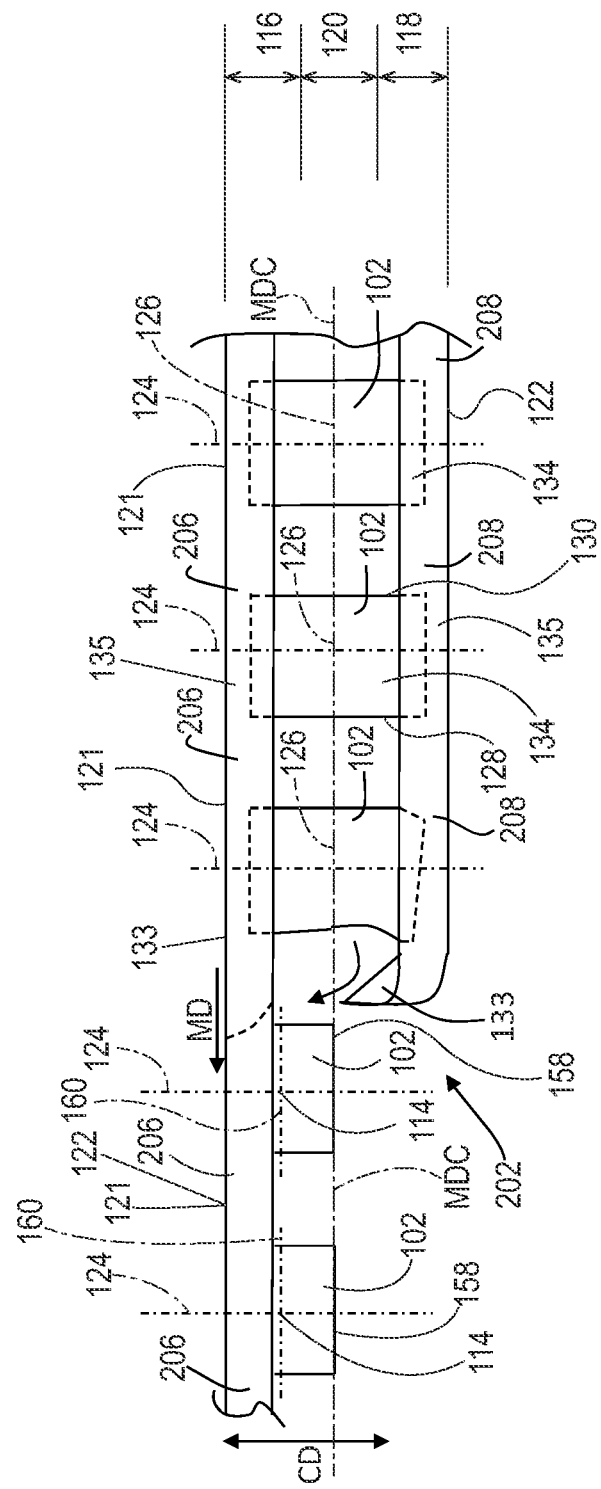
FIG. 4C is a schematic, plan view of a continuous length of diaper pants from FIG. 4A taken along line 4C-4C.

As shown in FIGS. 4A and 4C, the continuous length of absorbent articles 202 advances to a folding apparatus 212. At the folding apparatus 212, each chassis 102 may be folded in the cross direction CD along a lateral fold line 158 to place the first waist region 116, and specifically, the inner, wearer facing surface 132 into a facing, surface to surface orientation with the inner, wearer facing surface 132 of the second waist region 118. As shown in FIG. 4C, the first and second continuous waistbands 206, 208 may define an outer, garment facing surface 135 and an inner, wearer facing surface 133. Folding the chassis 102 also positions the inner, wearer facing surface 133 of the second waistband substrate extending between each chassis 102 into a facing relationship with the inner, wearer facing surface 133 of the first waistband substrate 206 extending between each chassis 102.

Figure 4D:
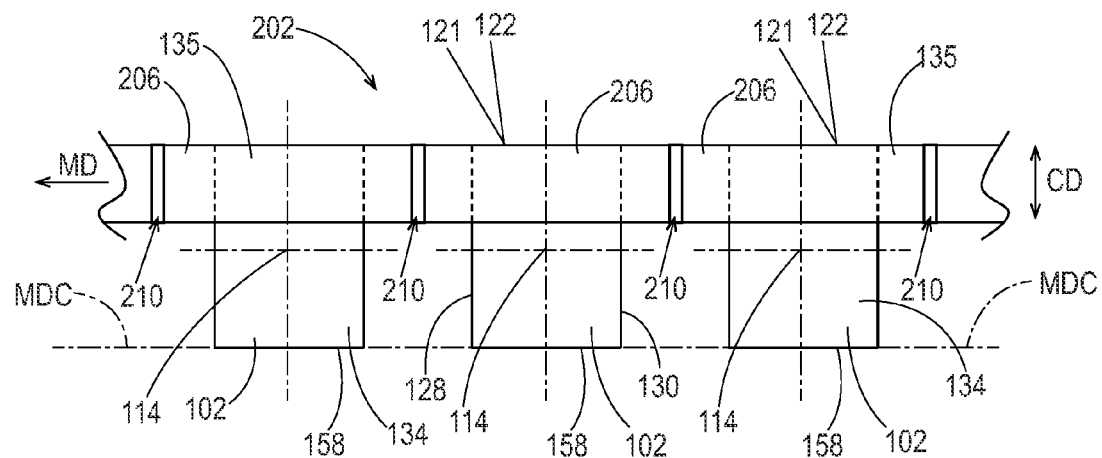
FIG. 4D is a schematic, plan view of a continuous length of folded diaper pants from FIG. 4A taken along line 4D-4D.

Referring to FIGS. 4A and 4D, the folded, continuous length of absorbent articles 202 may advance to the bonder apparatus 214. At the bonder apparatus 214, a portion of the first and second continuous waistband substrates 206, 208 extending between discrete chassis 102 may be bonded together to form bonded portions 210. It is to be appreciated that various types of bonder apparatuses and methods can be used to bond the second waistband substrate material 208 with the first waistband substrate material 206, such as the methods and apparatuses disclosed in U.S. Pat. Nos. 6,248, 195; 6,546,987; and 7,383,865, as well as U.S. Patent Publication No. 2012/0021186, published Jan. 26, 2012.

Figure 4E:
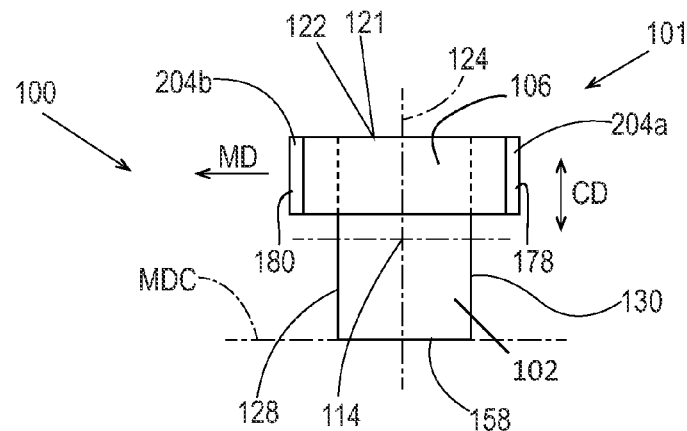
FIG. 4E is a schematic, plan view of a folded, discrete diaper pant from FIG. 4A taken along line 4E-4E.

As shown in FIG. 4A, a continuous length of absorbent articles 202 may advance from the bonding apparatus 214 to a cutter 216, shown in the form of a knife roll 218 for purposes of illustration. The cutter 216 cuts the bonded portions 210 along the cross direction CD to create a first side seam 204a on a folded, discrete diaper pant 101 and a second side seam 204b on a subsequently advancing folded diaper pant 101 as shown in FIG. 4E. The folded diaper pant 101 may define a folded, lateral centerline 160 that intersects the longitudinal centerline 124 of the diaper pant 101 at a center 114 of the folded diaper pant 101. The folded, lateral centerline 160 laterally bisects the folded diaper pant 101 such that the folded, lateral centerline 160 is equidistant from the front waist edge 121 and the lateral fold line 158. Subsequently, the folded diaper pant 101 is advanced to the transfer apparatus 220 where the folded diaper pant 101 may be rotated and shifted before advancing to downstream converting operations as shown in FIG. 4A.

Figure 4F:
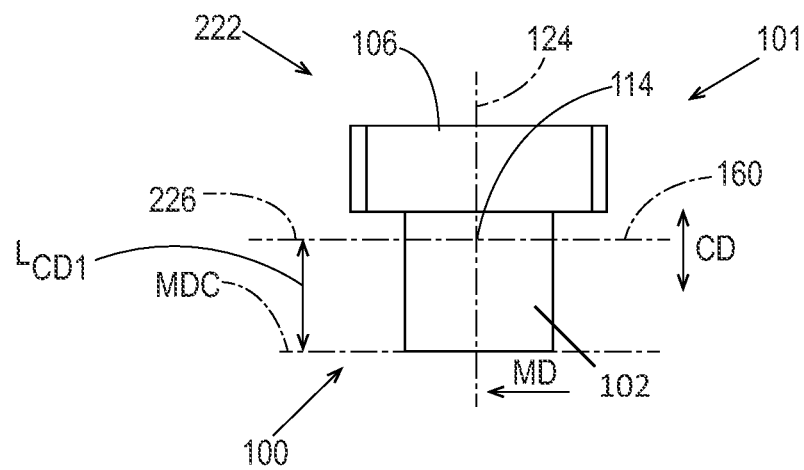
FIG. 4F is a schematic, plan view of a folded, discrete diaper pant from FIG. 4A taken along line 4F-4F.
Figure 4G:
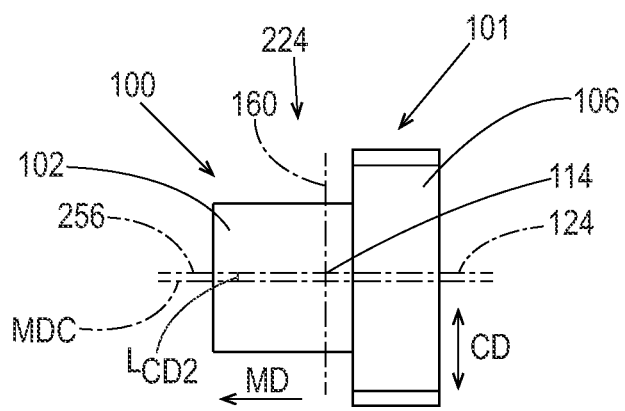
FIG. 4G is a schematic, plan view of a folded, discrete diaper pant from FIG. 4A taken along line 4G-4G.

The transfer apparatus 220 operates to change the orientation of the folded diaper pant 101 as the folded diaper pant 101 advances in the machine direction MD. With reference to FIGS. 4A, 4F, and 4G, the transfer apparatus 220 operates to change the orientation of the folded diaper pant 101 from a first orientation 222 to a second orientation 224. As shown in FIG. 4F, in the first orientation 222, the longitudinal centerline 124 of folded diaper pant 101 may extend in the cross direction CD and the center 114 of the folded diaper pant 101 may be located at a first cross-directional position 226. The first cross-directional position 226 may be located a first cross-directional length $L_{CD1}$ from the machine direction centerline MDC. As shown in FIG. 4G, in the second orientation 224, the longitudinal centerline 124 of the folded diaper pant 101 may extend in the machine direction MD and the center 114 of the folded diaper pant 101 may be located at a second cross direction position 256. The second cross direction position 256 may be different from the first cross direction position 226. As shown in FIG. 4G, the center 114 may be located at a second cross-directional length $L_{CD2}$ from the machine direction centerline MDC. It is to be appreciated that in some exemplary configurations, the center 114 of the folded diaper pant 101 may align with the machine direction centerline MDC. In such an exemplary configuration, the second cross-directional length $L_{CD2}$ may be zero.

Figure 5A:
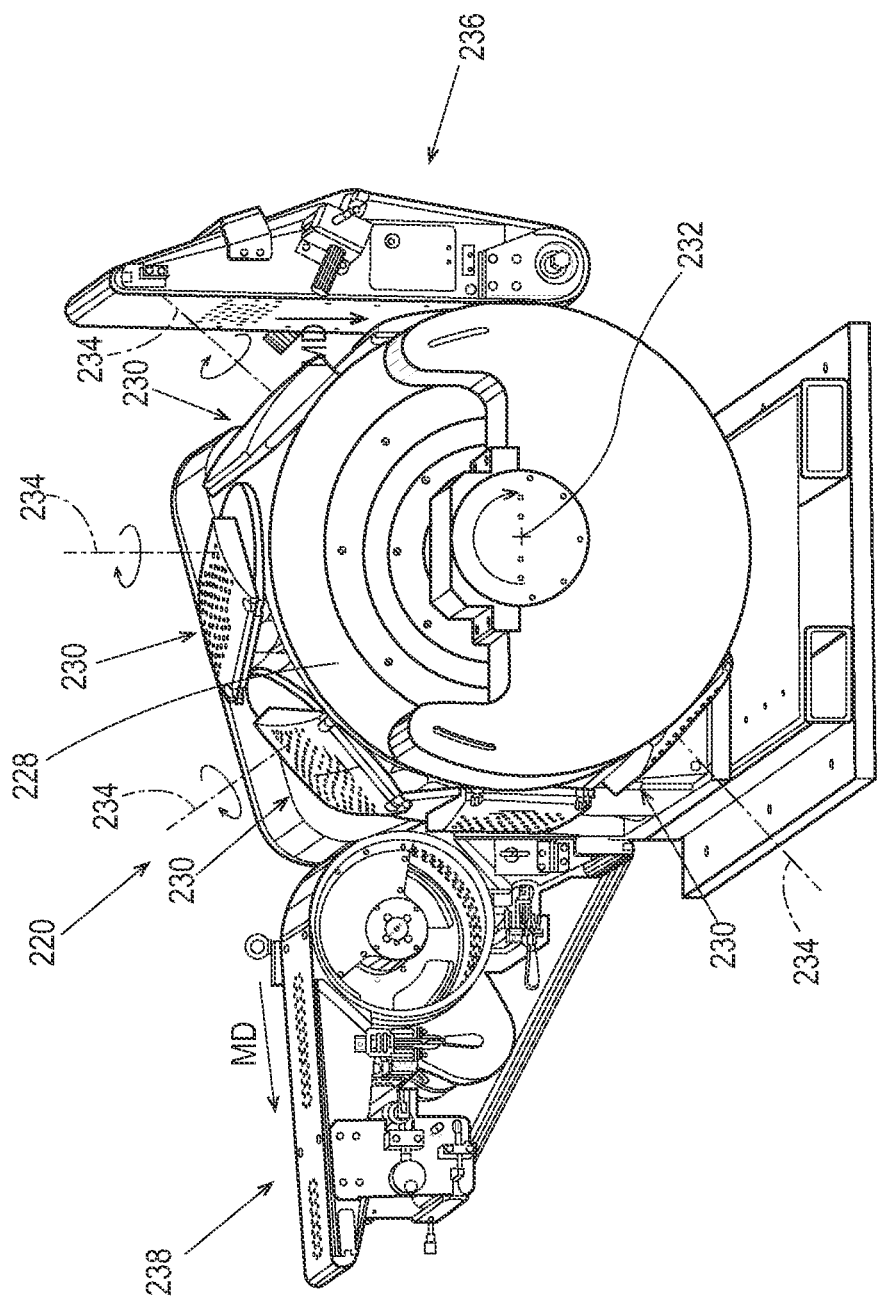
FIG. 5A is a perspective, side view of a transfer apparatus.
Figure 5B:
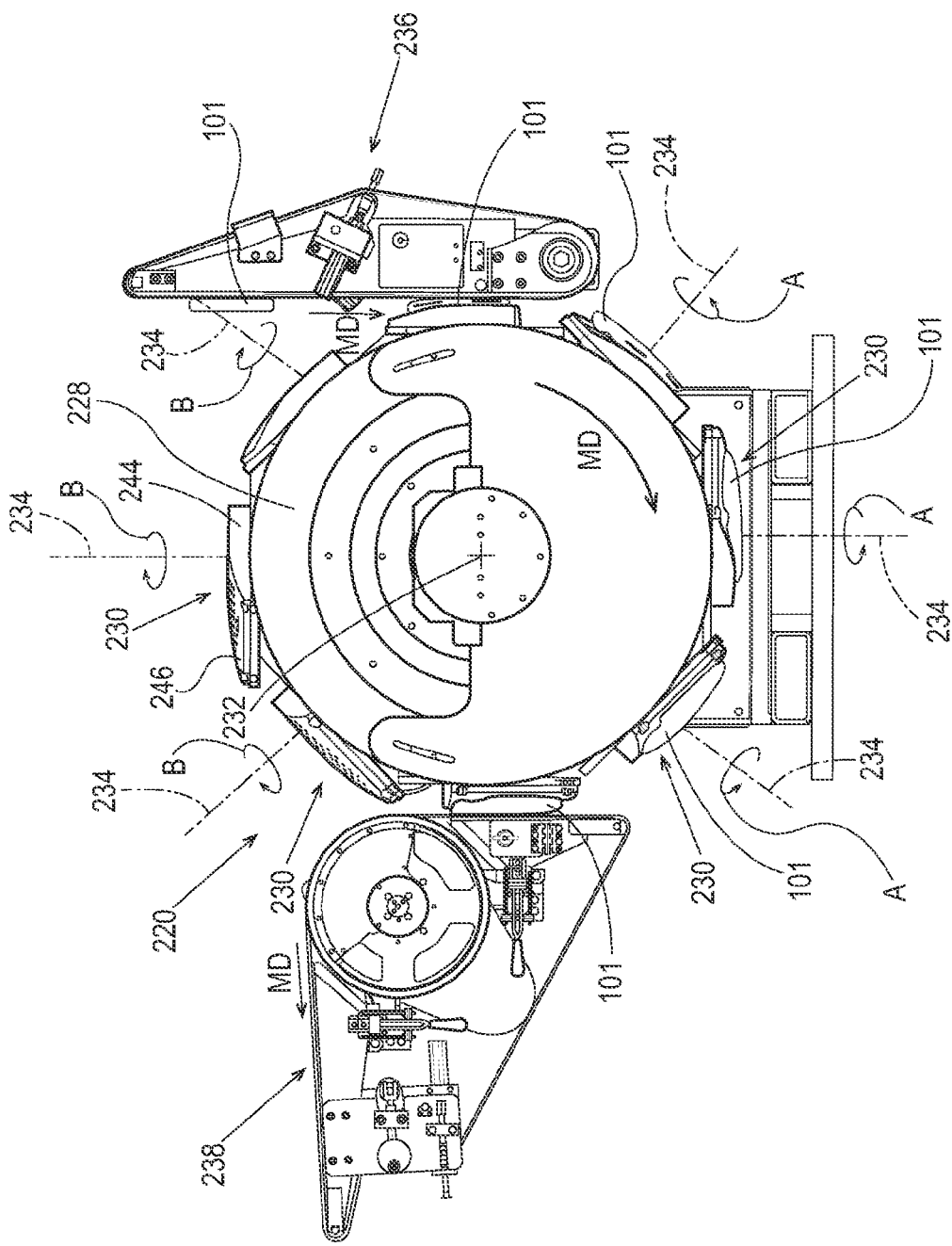
FIG. 5B is a front, elevation view of a transfer apparatus.

As shown in FIGS. 5A and 5B, the transfer apparatus 220 may include a frame 228 and a plurality of transfer members 230 connected with the frame 228. The frame 228 is adapted to rotate about a first axis of rotation 232 that extends in a first direction. The transfer members 230 are adapted to rotate about a second axis of rotation 234. The second axis of rotation 234 extends in a second direction that is different from the first direction of the first axis of rotation 232. The second axis of rotation 234 may be orthogonal to the first axis of rotation 232. Each transfer member 230 is configured to advance a folded diaper pant 101 from the first carrier apparatus 236 to the second carrier apparatus 238.

Figure 6:
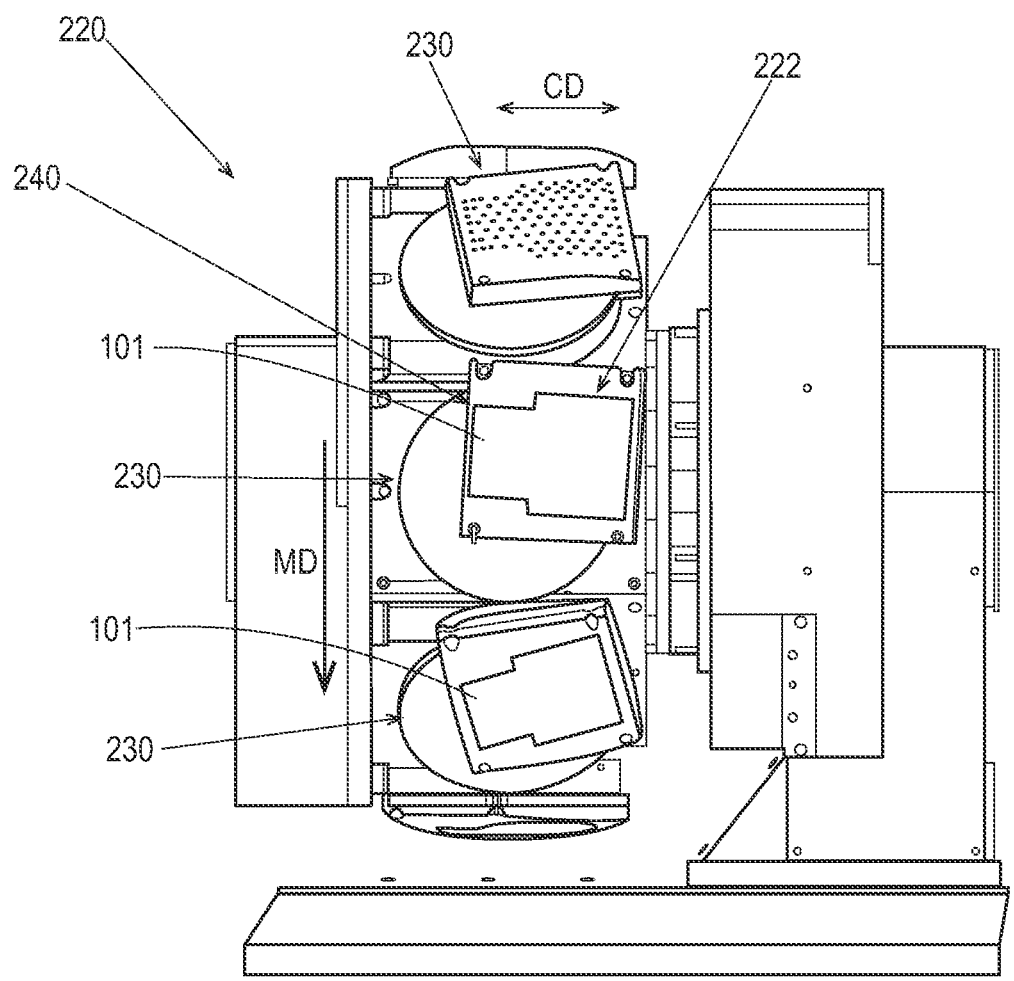
FIG. 6 is a side, elevation view of a transfer apparatus.
Figure 7:
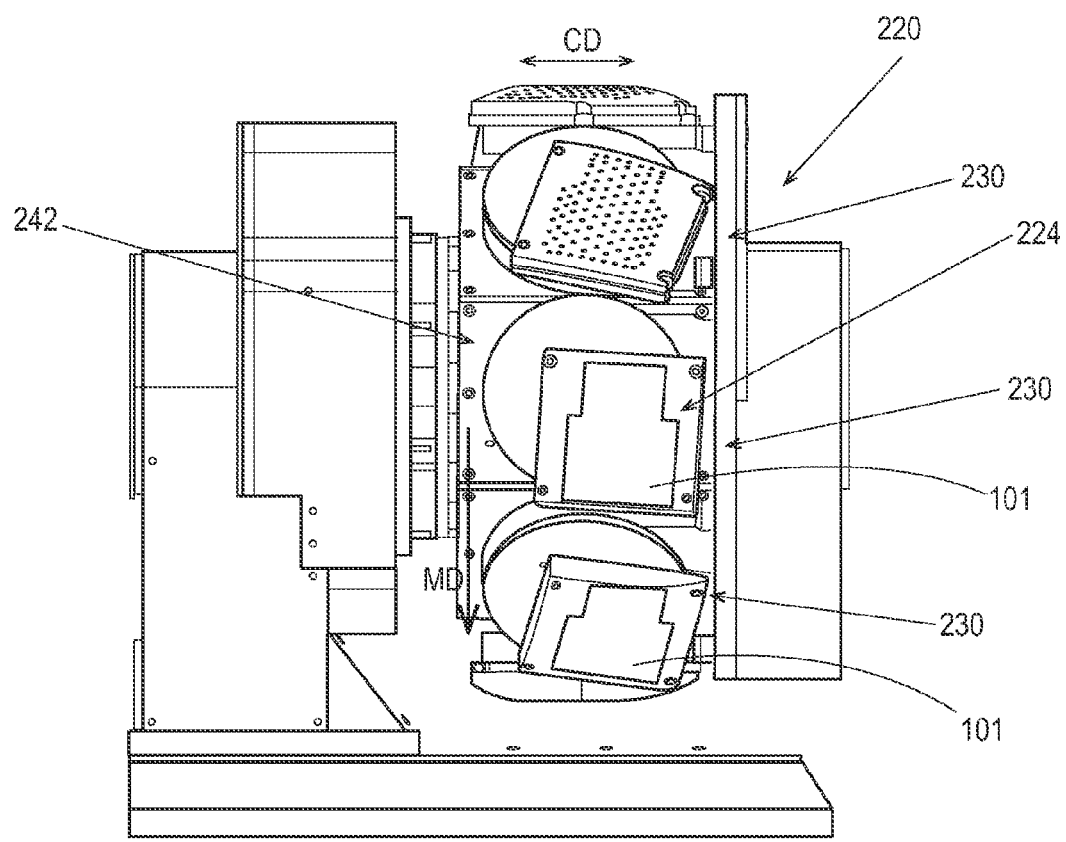
FIG. 7 is a side, elevation view of a transfer apparatus.

Referring to FIGS. 4A, 5A and 5B, in operation, the frame 228 rotates about the first axis of rotation 232 and the transfer member 230 rotates about the second axis of rotation 234. A folded diaper pant 101 advances on a first carrier apparatus 236 adjacent to the transfer apparatus 220. The folded diaper pant 101 is transferred from the first carrier apparatus 236 and onto the transfer member 230 as the transfer member 230 rotates adjacent to the first carrier apparatus 236. When the folded diaper pant 101 advances onto the transfer member 230, the folded diaper pant 101 is oriented in the first orientation 222 and the transfer member 230 is in the first position 240, such as shown in FIG. 6. The frame 228 continues rotating about the first axis of rotation 232 and the transfer member 230 rotates the folded diaper pant 101 about the second axis of rotation 234. The folded diaper pant 101 advances on the transfer member 230 until the transfer member 230 is positioned in a second position 242 and the folded diaper pant 101 is at the second orientation 224, such as shown in FIG. 7. The folded diaper pant 101 is then transferred from the transfer member 230 and advanced onto the second carrier apparatus 238 that is located adjacent to the transfer apparatus 220 as shown in FIG. 5A.

Figure 8:
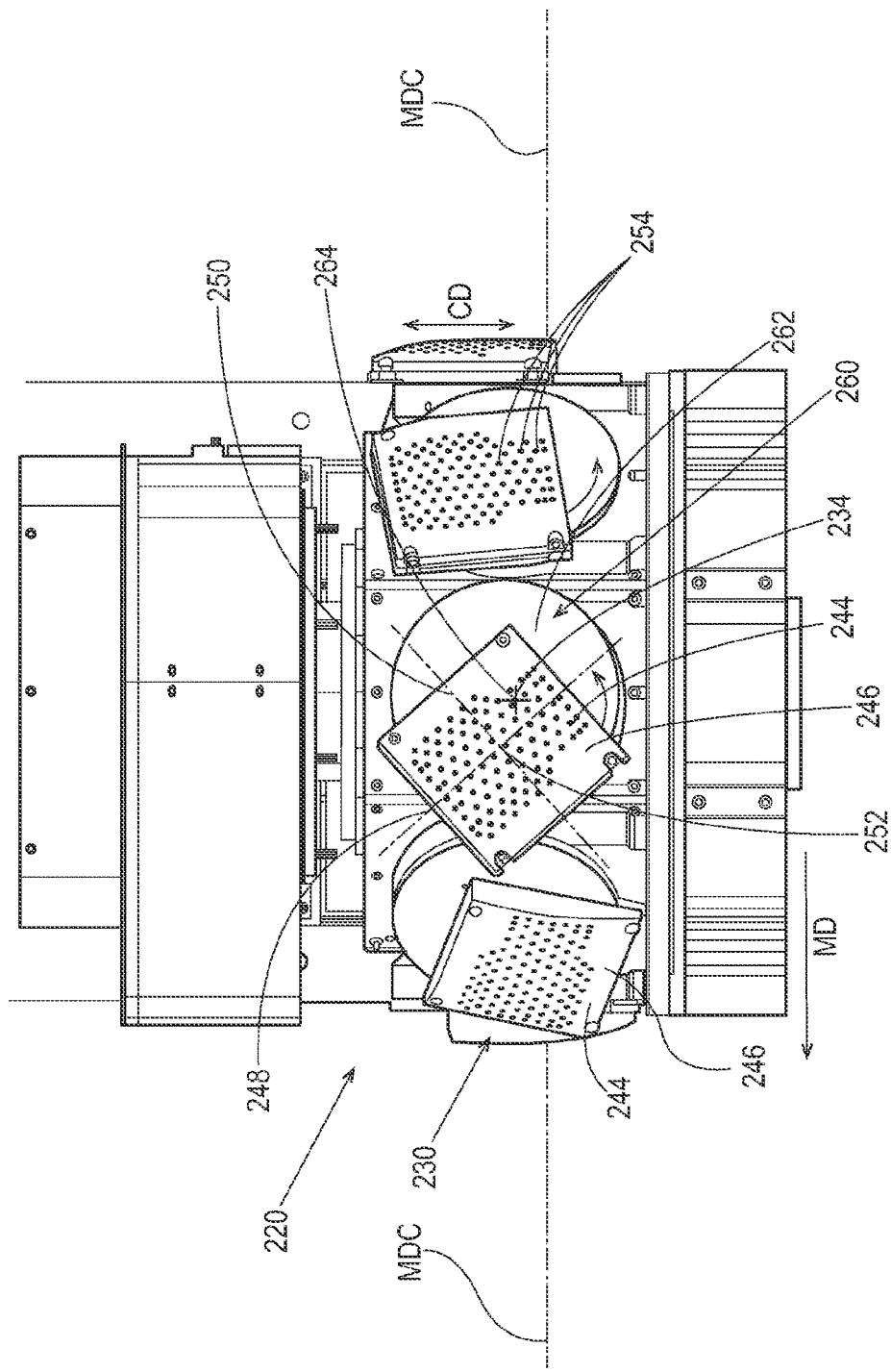
FIG. 8 is a bottom, plan view of a transfer apparatus.

Referring to FIGS. 5A and 8, each transfer member 230 may include a receiving member 244 having a receiving surface 246 located on an end of the transfer member 230 most distal from the first axis of rotation 232. The receiving surface 246 may be defined by a first centerline 248 and a second centerline 250 that intersect at a center 252 of the receiving surface 246. In some exemplary configurations, the center 252 of the receiving surface 246 may be offset from the second axis of rotation 234, such as shown in FIG. 8. The receiving surface 246 may be curved, or partially curved in one or more directions. However, in some exemplary configurations, the receiving surface may be flat, or substantially flat in one or more directions. As shown in FIG. 8, the receiving surface 246 may be substantially rectangular in shape; however, it is to be appreciated that the receiving surface may form various other shapes, such as squares, circles, or ovals for example. The receiving surface 246 may be configured to receive one or more folded diaper pant 101.

The transfer member 230 may also include a rotation assembly 260 that comprises a rotation member 262 as shown in FIG. 8. The rotation member 262 may be defined by a center 264. The rotation member 262 may be operatively connected with the receiving member 244. The receiving member 244 and the rotation member 262 may be separate elements, or in some exemplary configurations, the receiving member 244 and the rotation member 262 may be a single, continuous element. The second axis of rotation 234 may align with the center 264 of the rotation member 262, such as shown in FIG. 8. In such an exemplary configuration, the folded diaper pant may be positioned on the receiving surface 246 of the receiving member 244 such that the center of the folded diaper pant is substantially aligned with the center 252 of the receiving member 244. It is to be appreciated that in some exemplary configurations the center 264 of the rotation member 262 may be offset from the second axis of rotation 234. While it is shown in FIG. 8 that the rotation member 262 is substantially circular, it is to be appreciated that the rotation member may have various shapes and configurations.

With continuing reference to FIG. 8, the receiving surface 246 of the receiving member 244 may be configured to hold the discrete article in various ways. For example, the receiving surface 246 of the receiving member 244 may be configured to hold the discrete article thereto using fluid pressure, magnets, or an adhesive, for example. In some exemplary configurations, the receiving surface 246 may include a plurality of apertures 254 located in the receiving surface 246 of the receiving member 244. The apertures 254 may be in gaseous communication with a vacuum source for retaining the discrete articles on the receiving surface 246 of the receiving member 244 as the frame 228 and/or the transfer member 230 rotate about the first and second axis of rotation 232, 234, respectively. As shown in FIG. 8, the apertures 254 may be arranged into the shape of a folded diaper pant. However, it is to be appreciated that the apertures 254 may be arranged in various other configurations. The apertures 254 may also be used to apply a positive pressure to the discrete articles on the receiving surface 246. The positive pressure may be used, for example, to assist in the removal of the folded diaper pant from the receiving surface 246.

Figure 9:
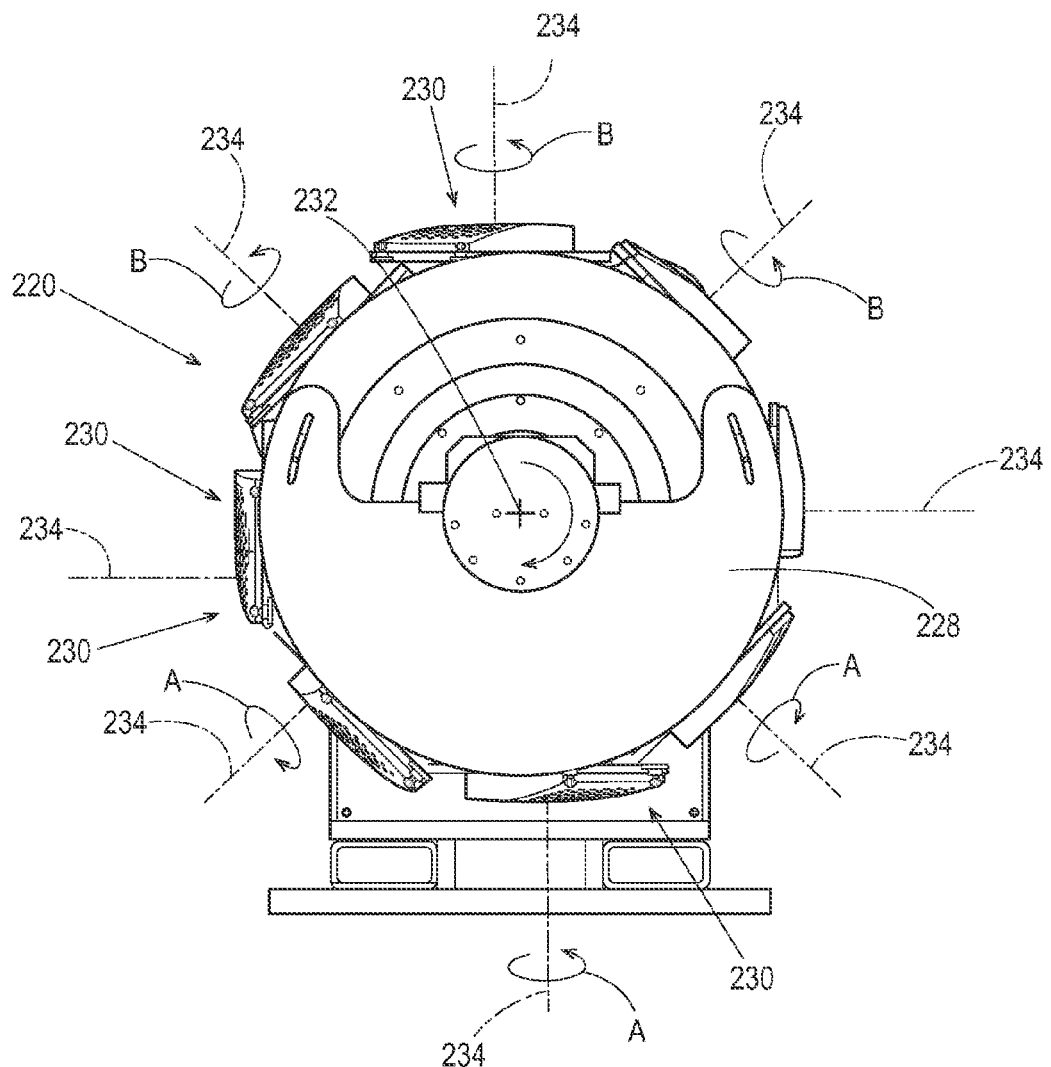
FIG. 9 is a front, elevation view of a transfer apparatus.

The transfer apparatus 220 may include eight transfer members 230 as shown in FIG. 9. However, it is to be appreciated that the transfer apparatus 220 may include various numbers of transfer members 230 that are each configured to rotate and shift a folded diaper pant from a first orientation to a second orientation.

With reference to FIGS. 5B, 6, 7, and 9, in some exemplary configurations, the transfer member 230 may rotate from a first position 240 to a second position 242 while advancing the folded diaper pant 101 from the first carrier apparatus 236 to the second carrier apparatus 238. As a result, the folded diaper pant 101 may rotate from the first orientation 222 to the second orientation 224. In some exemplary configurations, the transfer member 230 may continuously rotate from about 80° to about 100° from the first position 240 to the second position 242. In some exemplary configurations, the transfer member 230 may rotate 360° from the first position 240, through the second position 242, and back to the first position 240. As shown in FIG. 9, in some exemplary configurations, the transfer member 230 may rotate 90° in a first direction A about the second axis of rotation 234 and may be configured to subsequently rotate 90° in a second direction B about the second axis of rotation 234. Thus, the folded diaper pant 101 may be rotated at various rotation angles from the first orientation 222 shown in FIG. 4F to the second orientation 224 shown in FIG. 4G. For example, the folded diaper pant 101 may be rotated about 90° (for example, +/−5°), or between about 80° and 100° from the first orientation 222 to the second orientation 224. The rotation assembly 260 may be configured to rotate the receiving surface 246 of the receiving member 244 in various ways. For example, the rotation assembly 260 may be rotated using an electric servo motor, hydraulic or pneumatic actuators, or mechanical cams, for example.

Referring to FIG. 9, the frame 228 of the transfer apparatus 220 may be configured to continuously rotate about the first axis of rotation 232. The frame 228 may rotate at a constant angular velocity such that the speed at the receiving surface 246 is constant. In some exemplary configurations, the frame 228 may rotate at a variable angular velocity such that the speed at the receiving surface 246 is variable. In some exemplary configurations, the frame 228 may rotate about 180° to transfer a folded diaper pant from a first carrier apparatus 236 to the second carrier apparatus 238. The frame 228 may rotate at various rotation angles to transfer the folded diaper pant from a first carrier apparatus 236 to the second carrier apparatus 238. In such an exemplary configuration, the frame 228 may rotate a transfer member 230 about 180° about the first axis of rotation 232 in the same direction to pick up a subsequent folded diaper pant from the first carrier apparatus 236.

The first and second carrier apparatuses 236, 238 from and to which the folded diaper pants 101 are transferred may be rolls, drums, curved conveyors, linear conveyors, and/or discrete heads following a curvilinear path, for example. The first and second carrier apparatuses 236, 238 may be moving at a different surface velocity or at the same surface velocity. The transfer assembly apparatus 220 may pick up the folded diaper pant 101 from the first carrier apparatus 236 at the same velocity as is applied to the folded diaper pant 101 at the second carrier apparatus 238. The first and second carrier members 236, 238 may be configured to apply negative, vacuum pressure and/or positive, blow-off pressure to the folded diaper pants 101. In some exemplary configurations, the first and second carrier apparatuses 236, 238 may be configured to apply vacuum pressure to hold the discrete diapers pants 101 as the diaper pants advance on the first and second carrier apparatuses 236, 238. In some exemplary configurations, the first carrier apparatus 236 may be configured to apply positive, blow-off pressure to the discrete diaper pant 101 in order to assist the discrete diaper pant 101 in transferring from the first carrier apparatus 236 to the transfer apparatus 220.

In operation, the folded diaper pant 101 advances in the machine direction MD on the first carrier apparatus 236, such as shown in FIGS. 5B and 9. The folded diaper pant 101 is transferred from the first carrier apparatus 236 to the receiving surface 246 of the receiving member 244 as the frame 228 rotates about the first axis of rotation 232. The transfer member 230 is arranged at the first position 240 as the folded diaper pant 101 is transferred onto the receiving surface 246 of the receiving member 244, such as shown in FIG. 6. The folded diaper pant 101 advances onto the receiving surface 246 in a first orientation 222 where the longitudinal centerline 124 extends in the cross direction CD and the center 114 of the folded diaper pant 101 is located at a first cross-directional position 226, such as shown in FIG. 4F. With reference to FIGS. 5A, 5B, 7, and 9, the transfer member 230 concurrently rotates about the second axis of rotation 234 as the frame 228 rotates about the first axis of rotation 232. As a result, the folded diaper pant 101 rotates and the center of the folded diaper pant 101 shifts in the cross direction CD. The frame 228 continues to rotate about the first axis of rotation 232 and the transfer member 230 continues to rotate about the second axis of rotation 234 until the transfer member 230 is arranged in the second position 242. In the second position 242, the folded diaper pant 101 is oriented in a second orientation 224 where the longitudinal centerline 124 extends in the machine direction MD and the center 114 of the folded diaper pant 101 is located at a second cross-directional position 256 such as shown in FIG. 4G. The second cross-directional position may align with the machine direction centerline MDC.

As shown in FIGS. 5A and 5B, the transfer member 230 rotates about 90° about the second axis of rotation 234 in a first direction, A. Concurrently, the frame 228 of the transfer apparatus 220 rotates about 180° about the first axis of rotation 232 in a machine direction MD. Subsequently, the folded diaper pant 101 may be transferred from the transfer apparatus 220 to the second carrier apparatus 238. Vacuum may be intermittently interrupted in order to remove the folded diaper pant 101 from the receiving surface 246 of the receiving member 244. In some exemplary configurations, positive, blow-off pressure may be applied to the folded diaper pant 101 to assist the folded diaper pant 101 in transferring from the transfer apparatus 220 to the second carrier apparatus 238. The positive, blow-off pressure may be applied by a compressed air source or another fluid movement device through the apertures 254.

Figure 10:
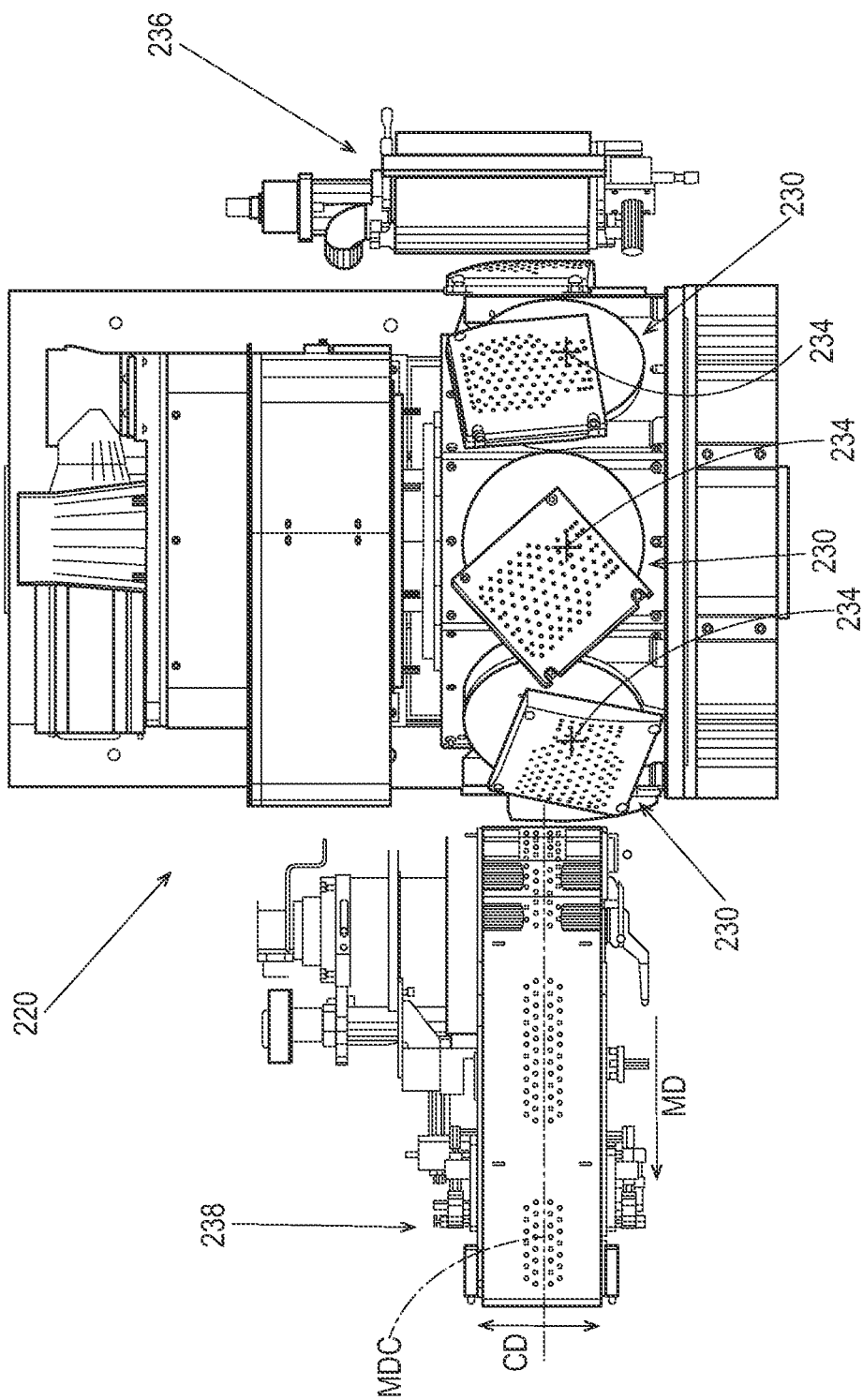
FIG. 10 is a top, plan view of a transfer apparatus.

As shown in FIGS. 4A, 9, and 10, once the folded diaper pant 101 is transferred to the second carrier apparatus 238, the frame 228 of the transfer apparatus 220 continues to rotate and the transfer member 230 rotates from the second position back to the first position in order to advance a subsequent folded diaper pant. The frame 228 may rotate about 180° about the first axis of rotation 232 to rotate the transfer member 230 from the second position back to the first position. In some exemplary configurations, the transfer members 230 rotate in a second direction B around the second axis of rotation 234 to move from the second position to the first position as shown in FIG. 9. In other exemplary configurations, the transfer members 230 may continue rotating in the first direction A around the second axis of rotation 234 from the second position back to the first position.

As shown in FIG. 11A, in a first orientation 222, the folded diaper pant 101 may be arranged such that the lateral fold line 158 is aligned with and extends along the machine direction centerline MDC and the center 114 of the folded diaper pant 101 is located in a first cross-directional position 226, away from the machine direction centerline MDC. The transfer member shown in FIG. 11A is in a first position 240. As shown in FIGS. 11B and 11C, the transfer member 230 rotates about the second axis of rotation 234 and the center 114 of the folded diaper pant 101 shifts in the cross direction CD. As shown in FIG. 11D, the folded diaper pant 101 is located in a second orientation 224 and the transfer member 230 is located in a second position 242. As a result of rotating the folded diaper pant 101 about the second axis of rotation 234, the folded diaper pant 101 may shift from the first orientation 222 to the second orientation 224 where the center 114 of the folded diaper pant 101 is aligned with the machine direction centerline MDC. In the second orientation 224 shown in FIG. 11D, the folded diaper pant 101 is also rotated such that the longitudinal centerline 124 extends in the machine direction MD.

In some exemplary configurations, the transfer member may rotate the folded diaper pant and then subsequently shift the cross-directional position of the center of the folded diaper pant. For example, the transfer member may be driven by two separate actuators; one actuator may rotate the rotation assembly of the transfer member, and the second actuator may shift the receiving member such that the cross-directional position of center of the folded diaper pant shifts.

The folded diaper pant may be positioned in various configurations with respect to the second axis of rotation. For example, as shown in FIGS. 11A-11D, the second axis of rotation 234 may align with the intersection of the longitudinal centerline 124 and the lateral fold line 158 of the folded diaper pant 101. In such an exemplary configuration, the longitudinal centerline 124 of the folded diaper pant 101 may align with the machine direction centerline MDC when the folded diaper pant 101 is rotated to the second orientation 224. It is to be appreciated that the folded diaper pant 101 may be arranged in various configurations at the second orientation 224 depending upon the desired orientation of the folded diaper pant 101 when the folded diaper pant 101 is transferred to the second carrier apparatus.

Figures 12A, 12B:
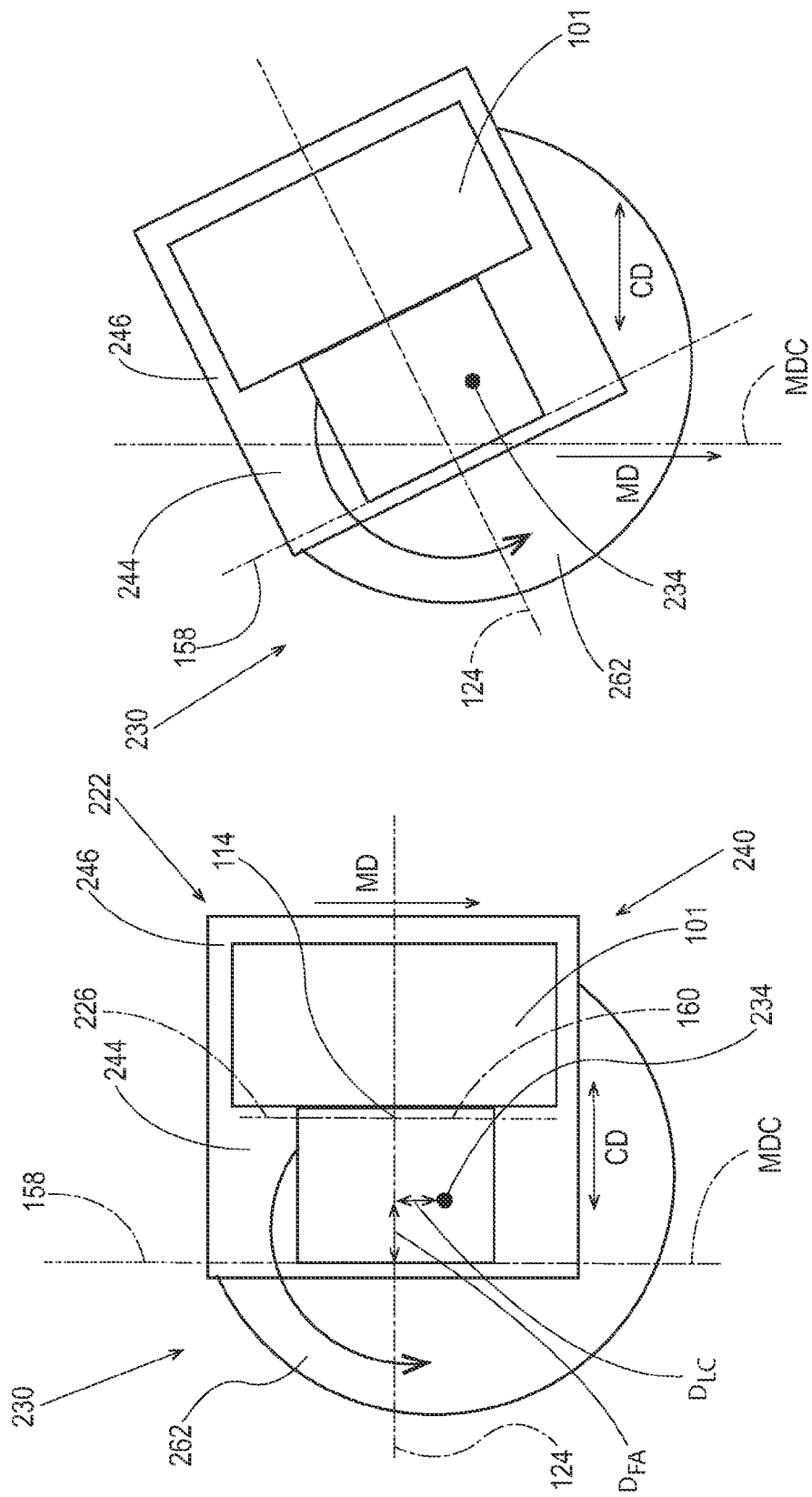
FIG. 12A is a schematic, plan view of an exemplary transfer member.
FIG. 12B is a schematic, plan view of an exemplary transfer member.
Figure 12D:
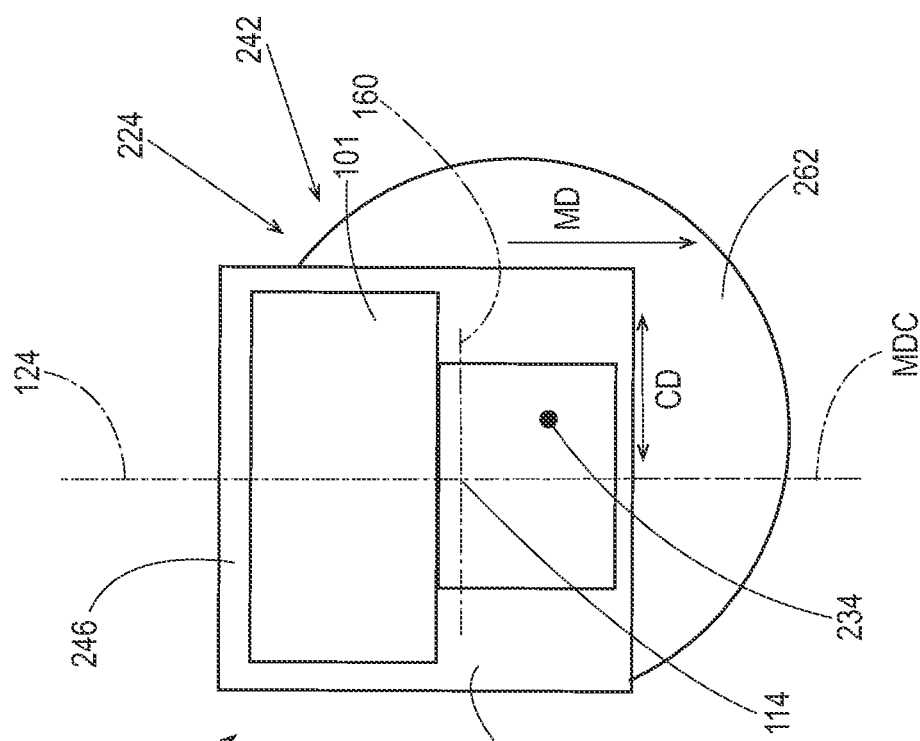
FIG. 12D is a schematic, plan view of an exemplary transfer member.
Figure 12C:
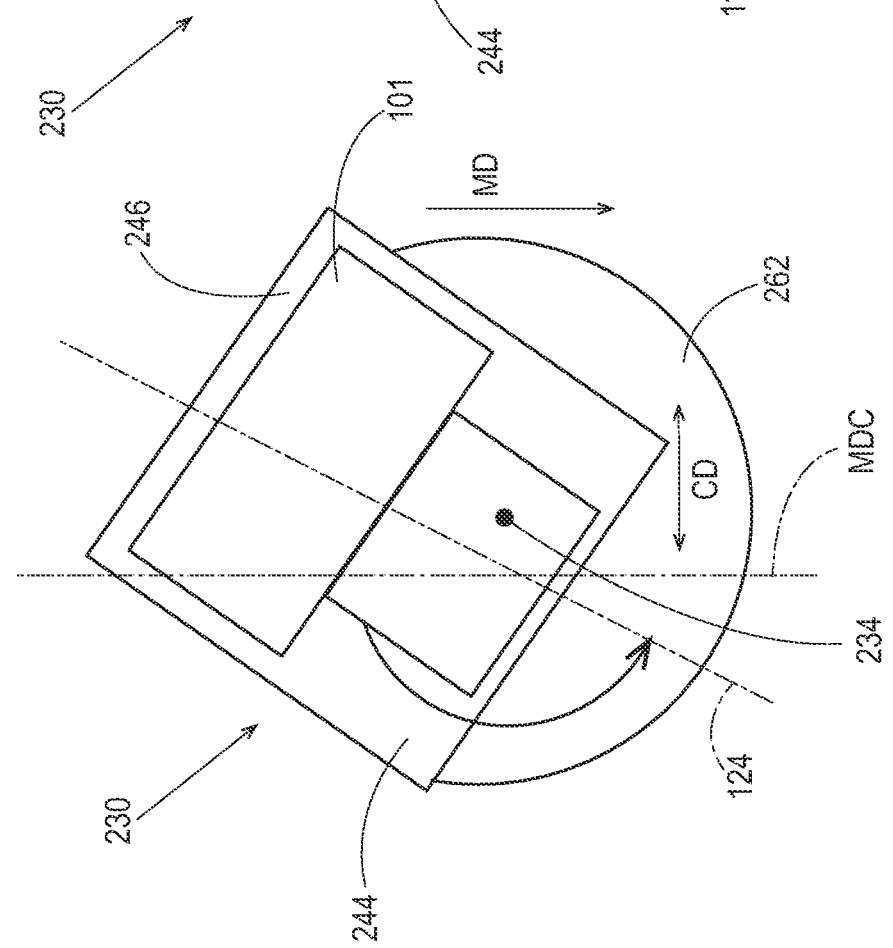
FIG. 12C is a schematic, plan view of an exemplary transfer member.

FIGS. 12A-12D show another exemplary configuration for a transfer member 230. As shown in FIG. 12A, the second axis of rotation 234 may be located a first distance $D_{FA}$ from the lateral fold line 158 and a second distance $ID_{LC}$ from the longitudinal centerline 124, where the first distance $D_{FA}$ and the second distance $ID_{LC}$ are equal. As shown in FIG. 12D, in such an exemplary configuration, the longitudinal centerline 124 of the folded diaper pant 101 may align with the machine direction centerline MDC when the folded diaper pant 101 is rotated to the second orientation 224. It is to be appreciated that in a configuration where the lateral fold line 158 is aligned with the machine direction centerline MDC at the first orientation 222, the second axis of rotation 234 may be aligned with various points on the folded diaper pant 101 where the first distance $D_{FA}$ and the second distance $D_{LC}$ are equal. In such configurations, the longitudinal centerline 124 may be positioned along the machine direction centerline MDC when the folded diaper pant 101 is rotated to the second orientation 224.

Referring to FIGS. 11A and 12A, the transfer methods and apparatuses disclosed herein may be configured to provide a relatively low rotational inertia $I_R$ to the transfer member 230 as the transfer member 230 rotates about the second axis of rotation 234. The transfer member 230 may be defined by a mass distribution that corresponds with a center of mass of the transfer member 230. If L is the distance from the second axis of rotation 234 and dm is the sum of the mass distribution of the transfer member 230, the rotational inertia $I_R$ of the transfer member 230 is:

$$I_R = \int L^2 dm$$

It is to be appreciated that the rotational inertia $I_R$ of the transfer member 230 is a function of the mass distribution of the transfer member 230 and also the center of mass of the transfer member. The closer the center of mass of the transfer member 230 is from the second axis of rotation 234, the lower the rotational inertia $I_R$ of the transfer member 230 may be. If $I_{cm}$ is the rotational inertia at the center of mass of the transfer member 230, M is the total mass of the transfer member 230, and D is the distance from the second axis of rotation 234 to the center of mass of the transfer member 230, the rotational inertia $I_R$ of the transfer member is:

$$I_R = I_{cm} + MD^2$$

In order to provide a relatively low rotational inertia $I_R$ to the transfer member 230 as the transfer member rotates about the second axis of rotation 234, the transfer member 230 may be configured in various ways. In some exemplary configurations, additional mass or counterweight may be added to the transfer member 230 to change the center of mass of the transfer member 230. In other exemplary configurations, the rotation member 262 may be configured such that center of the rotation member 262 is be positioned relatively nearer to the second axis of rotation. In yet other exemplary configurations, the receiving member 244 may be configured to be located relatively nearer to the second axis of rotation 234.

Figure 13A:
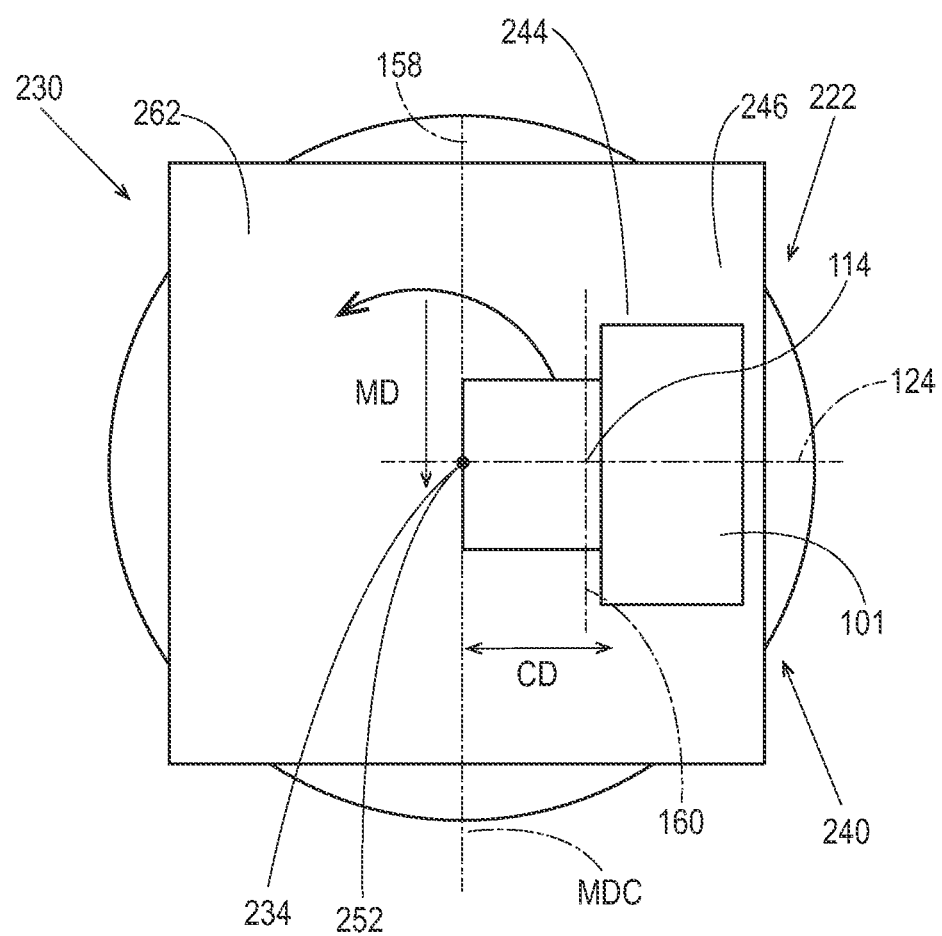
FIG. 13A is a schematic, plan view of an exemplary transfer member.
Figure 13B:
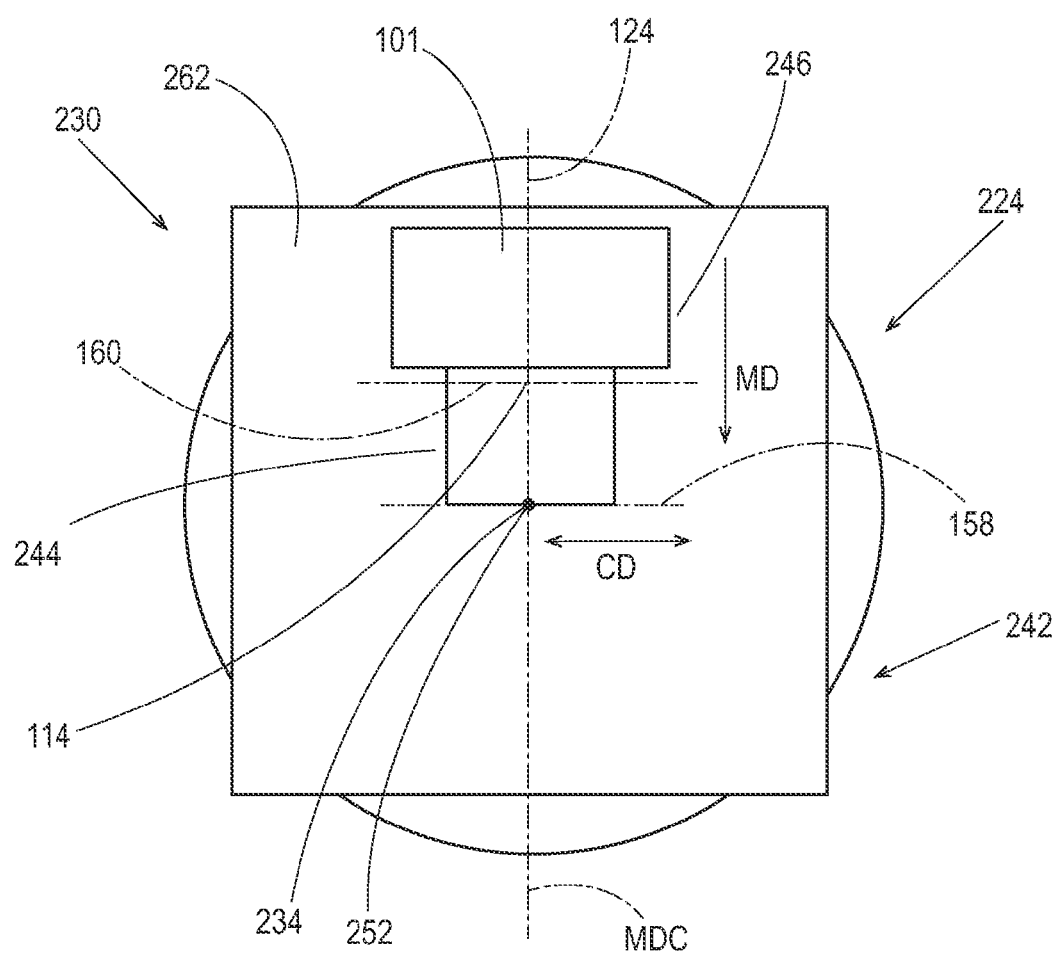
FIG. 13B is a schematic, plan view of an exemplary transfer member.

In some exemplary configurations, the center 252 of the receiving surface 246 may align with the second axis of rotation 234 as shown in FIGS. 13A and 13B. In such an exemplary configuration, the folded diaper pant 101 may cover only a portion of the receiving surface 246. The folded diaper pant 101 may be positioned on the receiving surface 246 such that the lateral fold line 158 and the longitudinal centerline 124 of the folded diaper pant 101 intersect at the second axis of rotation 234. It is to be appreciated that in the exemplary configurations shown in FIGS. 13A and 13B, the rotational inertia $I_R$ of the transfer member 230 may be relatively low as the center of mass of the transfer member 230 may be relatively near to the second axis of rotation 234.

Figure 14:
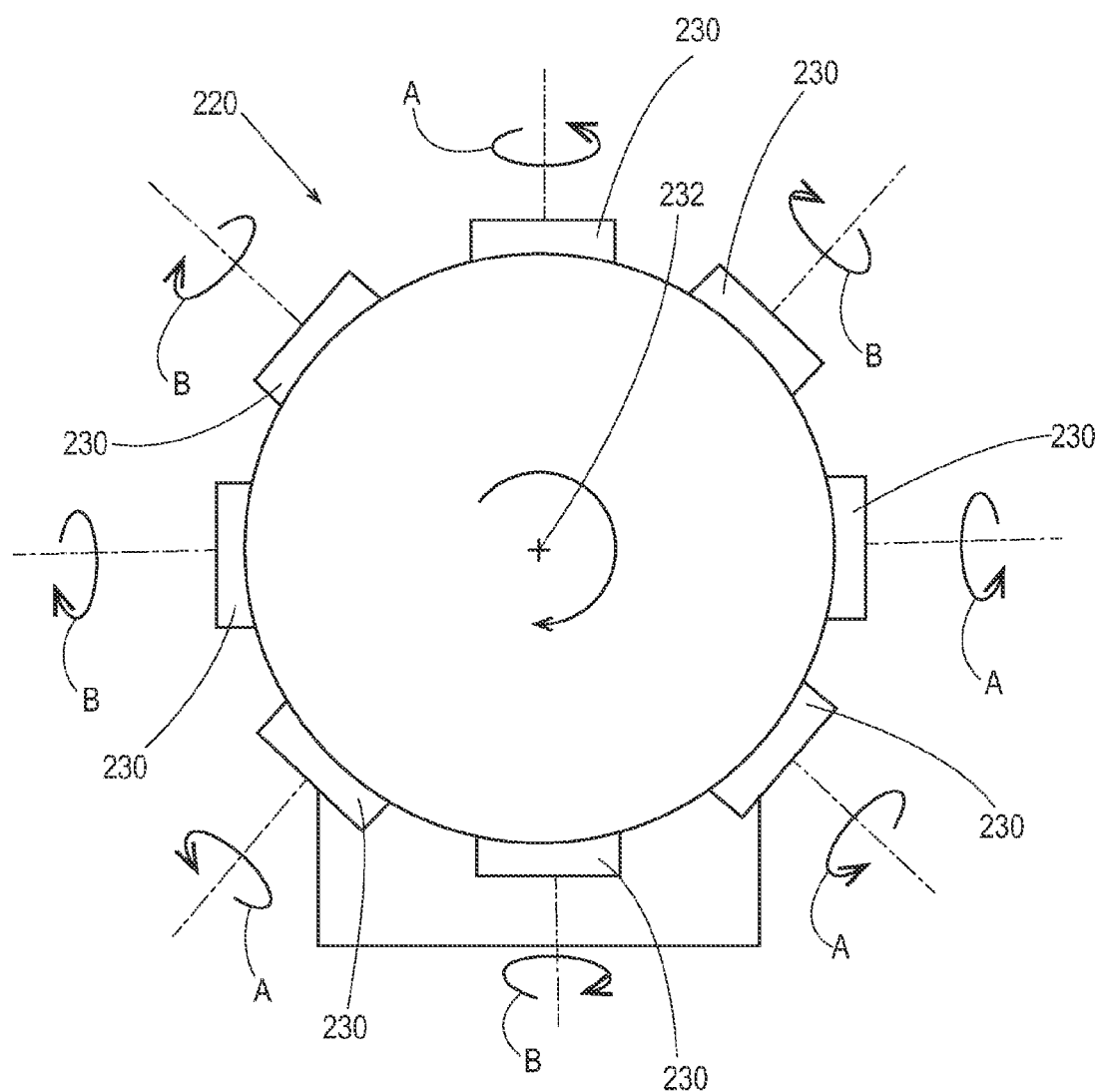
FIG. 14 is a schematic, front elevation view of a transfer apparatus.

In some exemplary configurations, one transfer member 230 may rotate in a first direction A and a subsequent transfer member 230 may rotate in a second direction B, such as shown in FIG. 14. As such, it is to be appreciated that a transfer apparatus 220 may be used to rotate one folded diaper pant in the first direction A and to rotate the next folded diaper pant in the second direction B.

For example, as disclosed in U.S. patent application Ser. No. 13/447,531, filed on Apr. 16, 2012; U.S. patent application Ser. No. 13/447,544, filed on Apr. 16, 2012; U.S. patent application Ser. No. 13/447,568, filed on Apr. 16, 2012; and U.S. patent application Ser. No. 13/447,585, filed on Apr. 16, 2012, the transfer member 230 may be radially displaced. As discussed with references to FIGS. 5B and 6-8, the transfer apparatus 220 may include a frame 228 and a plurality of transfer members 230, which are connected to the frame 228. The frame 228, including the transfer members 230, are adapted to rotate about a first axis of rotation 232. The transfer member 230 also rotates about a second axis of rotation 234. Further, the transfer member 230 may be radially displaced, such that the transfer member moves radially inward and radially outward relative to the first axis of rotation 232, as the transfer member 230 rotates about the first axis of rotation 232, as illustrated in FIG. 7 of U.S. patent application Ser. No. 13/447,531. The transfer member 230 may operatively engage, such as with followers, a track. The shape of the track may be such that it causes the transfer members 230 to be moved radially inwardly and outwardly.

While the methods and apparatuses disclosed herein operate to rotate and shift a folded diaper pant, it is to be appreciated that the methods and apparatuses disclosed herein may also be used in various other processes in the manufacture of absorbent articles. In one exemplary configuration, the methods and apparatuses disclosed herein may be used to rotate and shift discrete diaper chassis. The diaper chassis may comprise various components, such as a topsheet, backsheet, and an absorbent core. The transfer apparatus may be used to rotate and shift discrete chassis that are subsequently combined with continuous lengths of first and second waistband substrates. The methods and apparatuses disclosed herein may be used with the methods and apparatuses for rotating and repitching a discrete chassis disclosed in U.S. patent application Ser. No. 13/447,531, filed on Apr. 16, 2012; U.S. patent application Ser. No. 13/447,544, filed on Apr. 16, 2012; U.S. patent application Ser. No. 13/447,568, filed on Apr. 16, 2012; and U.S. patent application Ser. No. 13/447,585, filed on Apr. 16, 2012.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for changing the orientation of an absorbent article, the absorbent article defining a longitudinal centerline that intersects a lateral centerline at a center of the absorbent article, the method comprising the steps of:
    advancing the absorbent article in a first direction, wherein the absorbent article is oriented such that the longitudinal centerline extends in a second direction that is different from the first direction;
    positioning the absorbent article on a transfer member configured to rotate about a transfer axis of rotation, wherein the transfer member comprises a rotation member and a receiving surface attached to a portion of the rotation member, and wherein a center of the rotation member is aligned with the transfer axis of rotation, and wherein a center of the receiving surface and the center of the absorbent article is offset from the center of the rotation member;
    rotating the absorbent article about the transfer axis of rotation such that the longitudinal centerline extends in the first direction; and
    shifting the absorbent article such that the center of the absorbent article shifts in the second direction.

2. The method of claim 1, wherein the steps of rotating the absorbent article and shifting the absorbent article occur concurrently.

3. The method of claim 1 further comprising the steps of:
    rotating a frame about a first axis of rotation;
    rotating the transfer member about the first axis of rotation, wherein the transfer member is connected with the frame, wherein the transfer axis of rotation is orthogonal to the first axis of rotation, wherein the receiving surface is located on an end of the transfer member most distal from the first axis of rotation, wherein the transfer member is selectively rotatable from a first position to a second position, wherein the receiving surface is defined by a first centerline and a second centerline that intersect at the center; and
    advancing the absorbent article onto the receiving surface of the transfer member, wherein when the transfer member is in the first position, the absorbent article is in the first orientation, wherein when the transfer member is in the second position, the absorbent article is in the second orientation.

4. The method of claim 3, further comprising the step of radially displacing the transfer member with respect to the first axis of rotation as the transfer member rotates about the first axis of rotation.

5. The method of claim 3 further comprising the steps of:
    advancing the absorbent article on a first carrier apparatus;
    transferring the absorbent article from the first carrier apparatus to the transfer apparatus, wherein the transfer member is in a first position; and
    transferring the absorbent article from the transfer apparatus to a second carrier apparatus after the steps of rotating and shifting the absorbent article, wherein the transfer member is in a second position.

6. The method of claim 3, wherein the transfer member rotates from about 80 degrees to about 100 degrees from the first position to the second position.

7. The method of claim 3, wherein the receiving surface of the transfer member is curved, and wherein the rotation member comprises a circular plate.

8. The method of claim 3, wherein the center of the receiving surface of the transfer member is aligned with the center of the absorbent article.

9. The method of claim 3 further comprising the step of folding the absorbent article prior to the step of advancing the absorbent article onto the transfer apparatus.

10. The method of claim 9, wherein the step of folding comprises:

folding the chassis in a cross direction along a lateral fold line to place a first waist region into a facing orientation with a second waist region to form a folded absorbent article,
wherein the folded absorbent article has a lateral center line parallel to a first direction and a longitudinal centerline perpendicular to the first direction, and wherein the lateral centerline is a cross-directional length from a machine direction centerline.

11. The method of claim 1, wherein the first direction is a machine direction and the second direction is a cross direction.

12. A method for changing the orientation of an absorbent article, the absorbent article defining a longitudinal centerline that intersects a lateral centerline at a center of the absorbent article, the method comprising the steps of:
rotating a transfer apparatus about a first axis of rotation, wherein the transfer apparatus comprises a transfer member;
advancing the absorbent article in a first direction, wherein the absorbent article is oriented such that the longitudinal centerline extends in a second direction that is different from the first direction;
positioning the absorbent article on the transfer member configured to rotate about a second axis of rotation, wherein the transfer member comprises a rotation member and a receiving surface attached to a portion of the rotation member, and wherein a center of the rotation member is aligned with the second axis of rotation, and wherein a center of the receiving surface and the center of the absorbent article is offset from the center of the rotation member;
radially displacing the transfer member with respect to the first axis of rotation as the transfer member rotates about the first axis of rotation;
rotating the absorbent article about the second axis of rotation such that the longitudinal centerline extends in the first direction; and
shifting the absorbent article such that the center of the absorbent article shifts in the second direction.

13. The method of claim 12, wherein the step of radially displacing the transfer member comprises moving the transfer member radially inward and radially outward relative to the first axis of rotation.

14. The method of claim 13, further comprising the steps of:
advancing the absorbent article on a first carrier apparatus;
transferring the absorbent article from the first carrier apparatus to the transfer apparatus, wherein the transfer member is in a first position; and
transferring the absorbent article from the transfer apparatus to a second carrier apparatus after the steps of rotating and shifting the absorbent article, wherein the transfer member is in a second position.

15. The method of claim 14, wherein the transfer member is moved radially outward as the absorbent article is transferred from the first carrier apparatus to the transfer apparatus.

16. The method of claim 15, wherein the transfer member is moved radially outward as the absorbent article is transferred from the transfer apparatus to the second carrier apparatus.

17. The method of claim 12, wherein the transfer apparatus comprises a track extending about the first rotational axis, wherein the track comprises one or more projections extending radially outward form the first axis of rotation.

18. The method of claim 17, further comprising the step of engaging a portion of the track with one or more follower members extending from a portion of the transfer member.

19. The method of claim 12, wherein the absorbent article is a diaper pant, wherein the diaper pant defines a first waist region and a second waist region longitudinally separated by a crotch region, wherein the diaper pant is folded in the crotch region such that the first waist region is in a facing relationship with the second waist region.

20. A method for changing the orientation of an absorbent article, the absorbent article defining a longitudinal centerline that intersects a lateral centerline at a center of the absorbent article, the method comprising the steps of:
rotating a transfer apparatus about a first axis of rotation, wherein the transfer apparatus comprises a transfer member;
advancing the absorbent article in a first direction, wherein the absorbent article is oriented such that the longitudinal centerline extends in a second direction that is different from the first direction;
positioning the absorbent article on the transfer member configured to rotate about a second axis of rotation, wherein the transfer member comprises a rotation member and a receiving surface attached to a portion of the rotation member, and wherein a center of the rotation member is aligned with the second axis of rotation, and wherein a center of the receiving surface and the center of the absorbent article is offset from the center of the rotation member,
wherein the transfer apparatus is configured to rotate at a variable angular velocity such that the speed at the receiving surface is variable;
rotating the absorbent article about the second axis of rotation such that the longitudinal centerline extends in the first direction; and
shifting the absorbent article such that the center of the absorbent article shifts in the second direction.

* * * * *